US008618817B2

(12) United States Patent
Jakoby et al.

(10) Patent No.: US 8,618,817 B2
(45) Date of Patent: Dec. 31, 2013

(54) DEVICE AND METHOD FOR DETERMINING AT LEAST ONE PARAMETER OF A MEDIUM

(75) Inventors: Rolf Jakoby, Rosbach (DE); Martin Schuessler, Hoesbach (DE); Andreas Penirschke, Herborn (DE); Holger Maune, Kronberg am Taunus (DE)

(73) Assignee: Technische Universitaet Darmstadt, Darmstadt (DE)

( * ) Notice: Subject to any disclaimer, the term of this patent is extended or adjusted under 35 U.S.C. 154(b) by 942 days.

(21) Appl. No.: 12/514,308

(22) PCT Filed: Nov. 7, 2007

(86) PCT No.: PCT/DE2007/002001
§ 371 (c)(1),
(2), (4) Date: Jan. 14, 2010

(87) PCT Pub. No.: WO2008/055485
PCT Pub. Date: May 15, 2008

(65) Prior Publication Data
US 2010/0148804 A1    Jun. 17, 2010

(30) Foreign Application Priority Data
Nov. 8, 2006  (DE) .......................... 10 2006 052 637

(51) Int. Cl.
*G01R 27/26* (2006.01)

(52) U.S. Cl.
USPC ........... 324/663; 324/452; 324/453; 324/667; 324/668

(58) Field of Classification Search
USPC ................. 324/452, 453, 663, 667, 668, 71.1
See application file for complete search history.

(56) References Cited

U.S. PATENT DOCUMENTS 2,422,742 A * 6/1947 Odessey ......................... 324/667
4,286,208 A * 8/1981 French et al. ................. 324/663

(Continued)

FOREIGN PATENT DOCUMENTS

| DE | 44 44 248 A1 | 6/1996 |
| EP | 0 717 269 A2 | 6/1996 |
| GB | 2 214 640 A  | 9/1989 |

OTHER PUBLICATIONS

Goto, R., et al., "Composite Right/Left-Handed Transmission Lines Based on Conductor-Backed Coplanar Strips," IEICE Trans. Electron. E89-C(9):1306-1311, Sep. 2006.
Lai, A., et al., "Applications of Infinite Wavelength Phenomenon," Proceedings of the 36th European Microwave Conference, Manchester, United Kingdom, Sep. 10-15, 2006, pp. 937-939.
Penirschke, A., and R. Jakoby, "Microwave Sensor for Accurate Material Density Measurements of Gas/Solid Flows in Pipelines," Proceedings of the 36th European Microwave Conference, Manchester, United Kingdom, Sep. 10-15, 2006, pp. 443-446.

(Continued)

*Primary Examiner* — Jermele M Hollington
*Assistant Examiner* — Temilade S Rhodes-Vivour
(74) *Attorney, Agent, or Firm* — Christensen O'Connor Johnson Kindness PLLC

(57) ABSTRACT

The invention relates to a device for determining at least one parameter of at least one medium, said medium being introducible into at least one measuring path. An electric and/or electromagnetic field can be partially coupled into or out of the medium by passing at least one electric and/or electromagnetic signal into the measuring path. The measuring path comprises at least one line arrangement having at least two elementary cells arranged along the measuring path, said elementary cells comprising at least one electric path from at least one input to at least one output and comprising at least one respective capacitive element. The electrical properties of the capacitive element can by be modified by the medium. The electric and/or the electromagnetic signal can be applied to the input of a first elementary cell and the output of the first elementary cell can be connected to the input of a second elementary cell. The capacitive element of the respective elementary cell is arranged in the electric path of the first and second elementary cell. At least one inductive element connects the first elementary cell and the second elementary cell to a ground. The invention also relates to a method for determining a parameter of a medium.

51 Claims, 16 Drawing Sheets

(56) References Cited

U.S. PATENT DOCUMENTS

Figure 1:
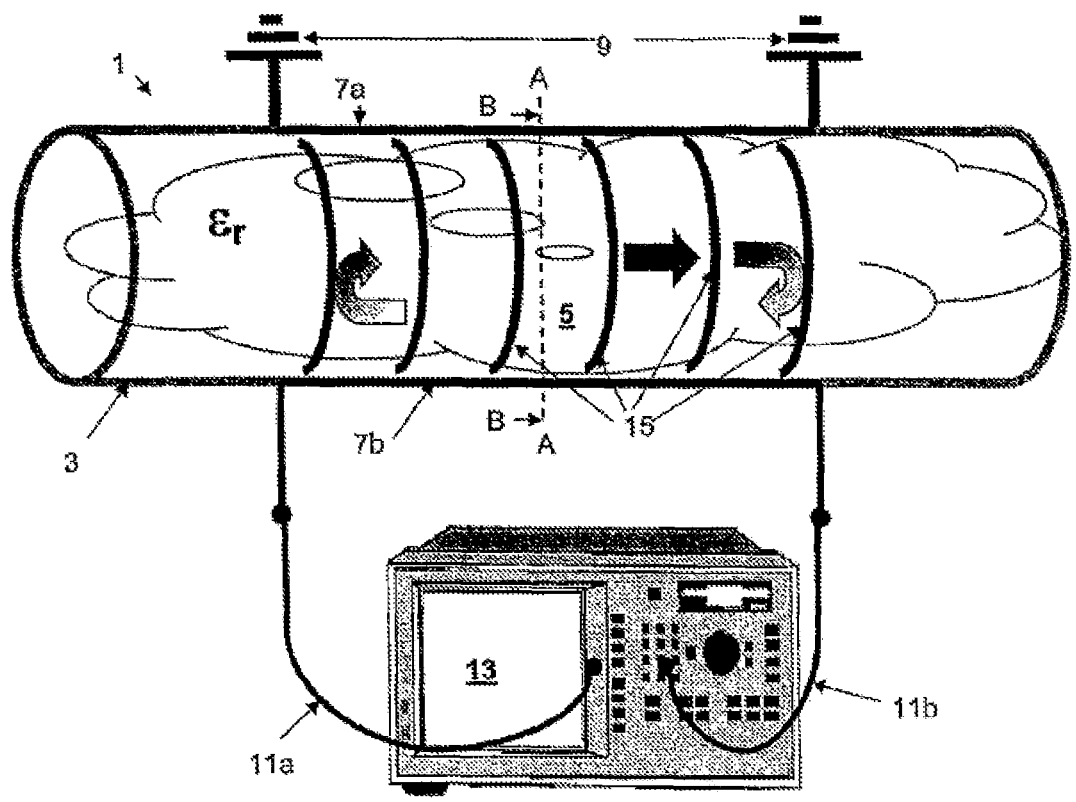
Figure 1:
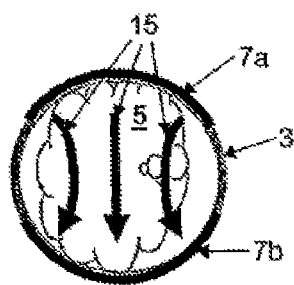

| | | | | |
|---|---|---|---|---|
| 5,844,415 | A * | 12/1998 | Gershenfeld et al. | 324/663 |
| 6,320,393 | B1 * | 11/2001 | Yasui et al. | 324/663 |
| 6,323,632 | B1 * | 11/2001 | Husher et al. | 324/71.1 |
| 6,333,691 | B1 * | 12/2001 | Janus | 340/552 |
| 6,859,141 | B1 * | 2/2005 | Van Schyndel et al. | 340/562 |
| 7,239,150 | B2 * | 7/2007 | Troxler et al. | 324/643 |
| 7,288,941 | B2 * | 10/2007 | Redko et al. | 324/450 |
| 7,629,797 | B2 * | 12/2009 | Tai et al. | 324/684 |
| 8,150,633 | B2 * | 4/2012 | Burke et al. | 702/19 |
| 2004/0155667 | A1 * | 8/2004 | Kesil et al. | 324/663 |
| 2005/0194982 | A1 * | 9/2005 | Urquidi | 324/661 |
| 2006/0017123 | A1 * | 1/2006 | Ghallab et al. | 257/414 |
| 2006/0066422 | A1 | 3/2006 | Itoh | |
| 2006/0186898 | A1 * | 8/2006 | Ichimura et al. | 324/663 |

OTHER PUBLICATIONS

Penirschke, A., et al., "New Microwave Flow Sensor Based on a Left-Handed Transmission Line Resonator," IEEE MTT-S International Microwave Symposium, Honolulu, Hawaii, Jun. 3-8, 2007, pp. 393-396.

Penirschke, A., et al., "Novel Integrated Coaxial Line to Cylindrical Waveguide Directive Couplers in Pipelines for Process Monitoring Applications," IEEE MTT-S International Microwave Symposium, Long Beach, California, Jun. 12-17, 2005, pp. 1203-1206.

International Search Report dated Mar. 13, 2008, issued in corresponding PCT/DE2007/002001, filed Nov. 7, 2007.

English Translation of International Preliminary Report on Patentability, issued Feb. 3, 2009, in corresponding International Application No. PCT/DE2007/002001, filed Nov. 7, 2007, 7 pages.

\* cited by examiner

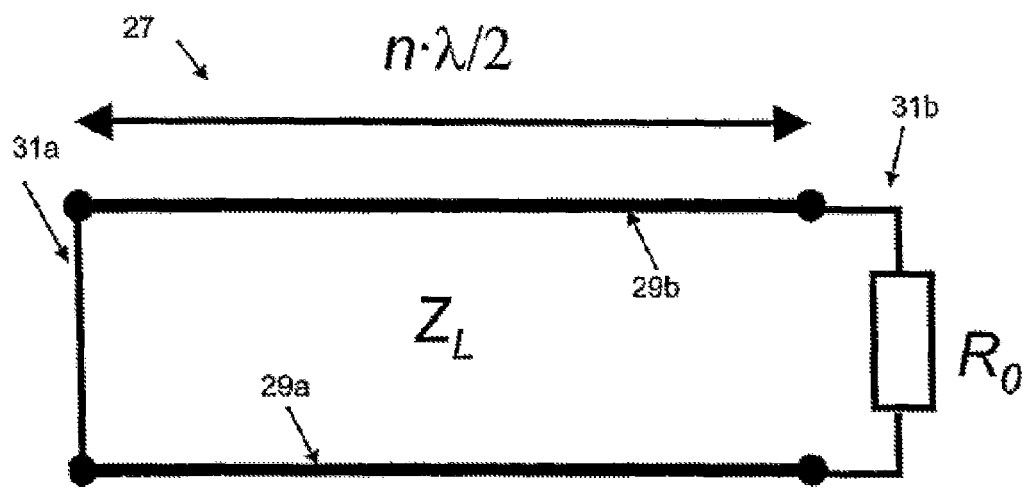
Fig. 8
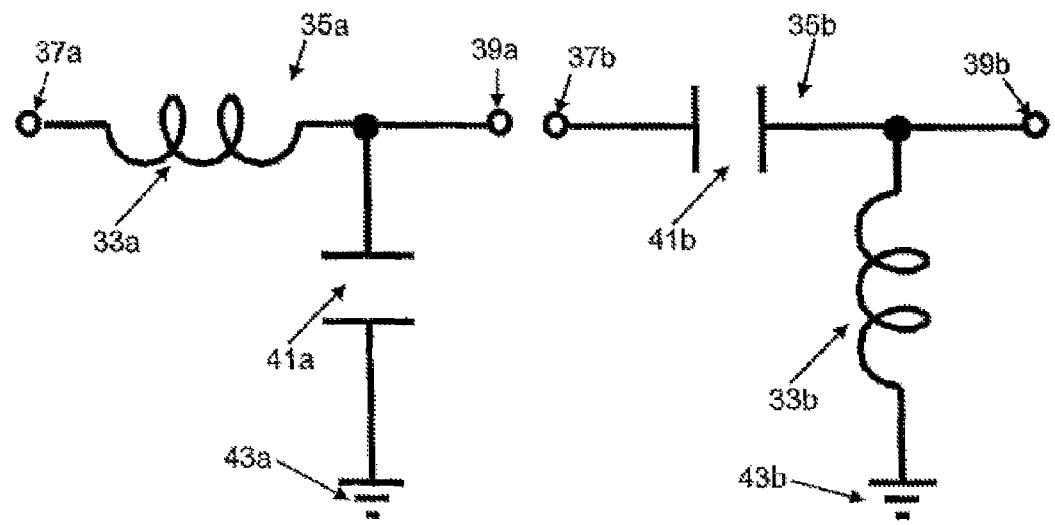
Fig. 9 a)                    Figure 9 b)

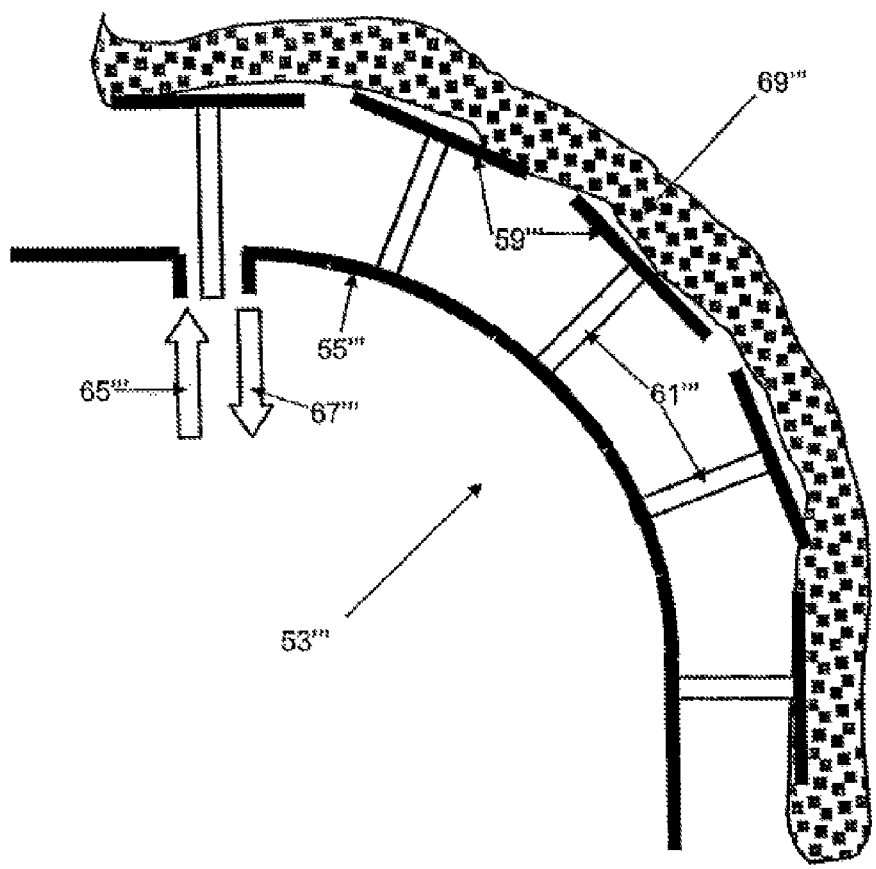
Fig. 14
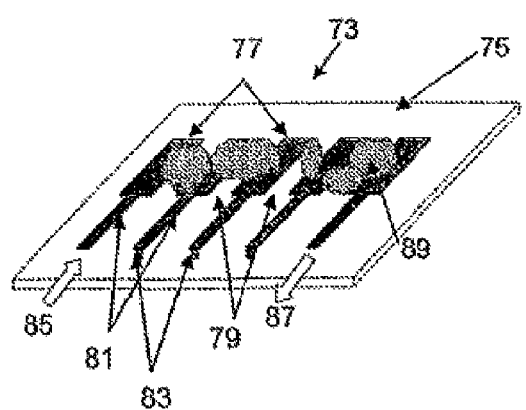 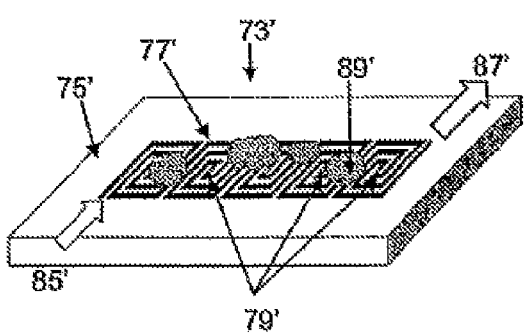
Fig. 15 a)　　　Fig. 15 b)

DEVICE AND METHOD FOR DETERMINING AT LEAST ONE PARAMETER OF A MEDIUM

The present invention relates to a device comprising a measuring path having a line system which has at least two elementary cells situated along the measuring path, each elementary cell comprising an electrical path from at least one input to at least one output, wherein the elementary cells each comprise at least one capacitive element, and the device includes a generator for generating an electrical and/or electromagnetic signal, the electrical and/or electromagnetic signal being supplied to the input of a first elementary cell, and the output of the first elementary cell being connected to the input of a second elementary cell, and the capacitive element of the respective elementary cell being situated in the electrical path of the first and second elementary cells, and in each case at least one inductive element connects the electrical path of the first elementary cell and of the second elementary cell to an electrical ground, and further relates to a method for determining a parameter of a medium or material, in particular by use of the device according to the invention.

Microwaves, for example, are used to investigate various properties of stationary or moving fluids, liquids, or solid media. For this purpose a microwave signal, for example, may be radiated through the medium. For moving media, one possibility is to inject microwave signals into the medium in a defined segment of a conveying path, and to conduct the microwave signals from the medium at the end of the measuring path. A measuring system may then be provided in this region. The portion of the microwave signal which is not emitted in the intended direction, i.e., in particular which is not detected by the measuring system in the desired manner, is referred to as an interference signal. Interference signals result, for example, from losses during injection, unwanted reflections, and the signal portion which is emitted in the opposite direction from the desired direction of propagation.

When conveying tubes are used to transport a moving medium or conveyed material, in principle the penetration of the conveyed material with microwaves should occur in the conveying direction and orthogonally with respect to the conveying direction. However, if the microwave signal is to be introduced into the measuring path in the conveying direction without disturbing the material flow, this results in difficulties in coupling in and coupling out the microwave signal.

The determination of properties of the medium by use of microwave radiation is fundamentally based on the following principle. A change in the material density causes a change in the effective permittivity in the conveying tube, and thus, a change in the amplitude and phase position of the signal coupled out. By use of the relationships (described below) between the effective permittivity of the medium in the conveying tube and the permittivity of the concentrated medium, the amplitude and the phase position of the microwave signal coupled out may be used to draw conclusions concerning the material properties of the medium, such as the density of the medium in the conveying tube.

One device for contact-free measurement of the mass distribution using microwaves is known from DE 44 44 248 A1, for example. Essentially, the absorption of a microwave which penetrates into the interior of the tube through slits in a tube wall is measured. The microwaves are injected from a cavity resonator, and by use of antennas the transmitted portion of the supplied microwave is measured. Since a portion of the supplied microwave is absorbed by a material which is guided through the measuring apparatus via a tube, with assistance from the antennas conclusions may be drawn concerning the type of material inside the tube.

A method and a device which make use of the propagation of electromagnetic waves in electrically bounded structures (waveguides) for determining material densities are known from EP 0 717 269 A2. In the cited document, a microwave signal is introduced into a conveying tube via injection holes and, after a defined path length, is coupled out of the conveying tube. The disadvantage of this method is the nondirectional coupling in and out of the signal. As a result of the coupling opening, the efficiency, i.e., the proportion of the useful signal compared to the necessary microwave power, is very low. Furthermore, pulsed signals must be used in order to apply reflected signal portions outside the measuring path during time intervals in which measurement is not conducted.

US 2006/0066422 A1 discloses a resonator for wireless transmission of an electromagnetic signal, the resonator being operated for signal transmission and signal reception, preferably in a zeroth-order resonance mode.

A further measuring device is known from GB 2 214 640 A. This document discloses a system for tomographic imaging of the distribution of flowing materials. Metal plates are mounted on an electrically nonconductive tube section. By use of a complex measured value recording and evaluation circuit, the capacitance values between all possible pairs of the metal plates are measured and determined. As a result of the relatively small changes in the concentration of the medium between the particular pairs of metal plates, and thus in the relative permittivity to be measured, in this method capacitance values must be measured in the range of a few femtofarads. Resolution of such low capacitances is possible only by using highly sensitive temperature-stabilized evaluation circuits, which are very costly and also are at the resolution limit for the differential capacitance measuring instruments which are currently possible. A further disadvantage of this prior art is that an increase in the capacitance, and therefore an increase in the sensitivity of this method, is possible only by reducing the tube diameter or by enlarging the surface area of the metal plates.

Furthermore, the devices known from the prior art do not allow determination of a velocity of a medium in a measuring path, or the quantitative determination of a mass flow of the medium through the measuring path. For this purpose additional mechanical, acoustic, or electrostatic sensors are used to determine a mass flow of bulk material or liquid through a line.

The measurement principle of measuring systems known from the prior art is explained below with reference to FIGS. 1a) through 8.

FIGS. 1a), 1b), and 2 illustrate the design principle of a device known from the prior art, for example from GB 2 214 640 A, for determining a parameter of a medium, in the form of a measuring apparatus or measuring system 1, which is implemented as a line resonator for measuring the dielectricity of an unknown material, or for determining the material density of a known material. FIG. 1a) shows a longitudinal section, FIG. 1a) shows a sectional view along axis A-A from direction B in FIG. 1b), and FIG. 2 shows a perspective view of a portion of the measuring system 1. The measuring system 1, in particular as seen in FIG. 1a), includes a conveying line or conducting unit in the form of a tube 3. The tube 3 contains a material or medium 5 to be investigated, for example in the form of a fluid or a bulk material, which in particular flows through the tube 3. The medium 5 has a (relative) dielectric constant $\in_r$. In the region of the oppositely situated wall of the tube 3, metal plates which act as capacitor plates 7a, 7b are provided, in particular mounted, on the wall. Capacitor plate 7a is connected to a ground 9, whereas capacitor plate 7b is connected to two lines 11a, 11b, in particular in the form of coaxial cables. Using a measuring circuit in the form of a network analyzer 13, an electromagnetic signal is fed through the line 11a into capacitor assembly 7a, 7b by supplying alternating voltage at a frequency f. After this signal has passed through the system along the tube 3, an output signal is sent back to the network analyzer 13 via the line 11b. In the resonator structure formed by the two capacitor plates 7a, 7b and the interspace (the interior of the tube 3), electromagnetic oscillation may thus be generated whose resonance frequency is a function of the geometry of the resonator and the dielectricity $\in$ and the permeability µ of the medium 5 in the tube 3. The electrical field 15 generated by the capacitor plates 7a, 7b is influenced by the properties of the introduced medium 5.

Figure 3:
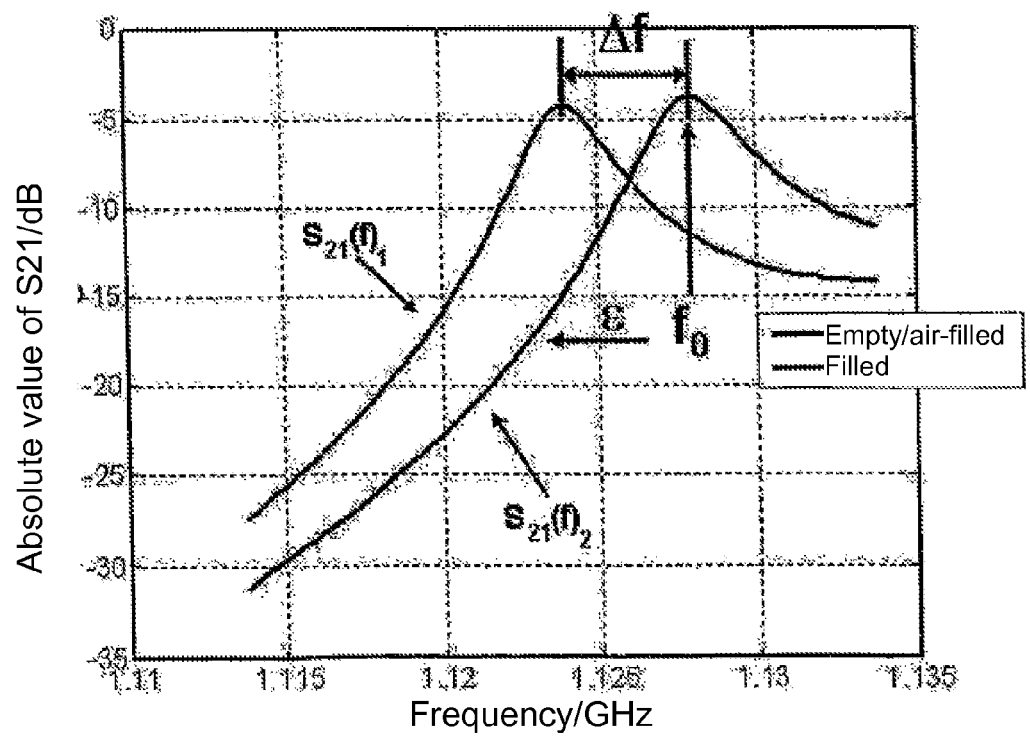
Figure 4:
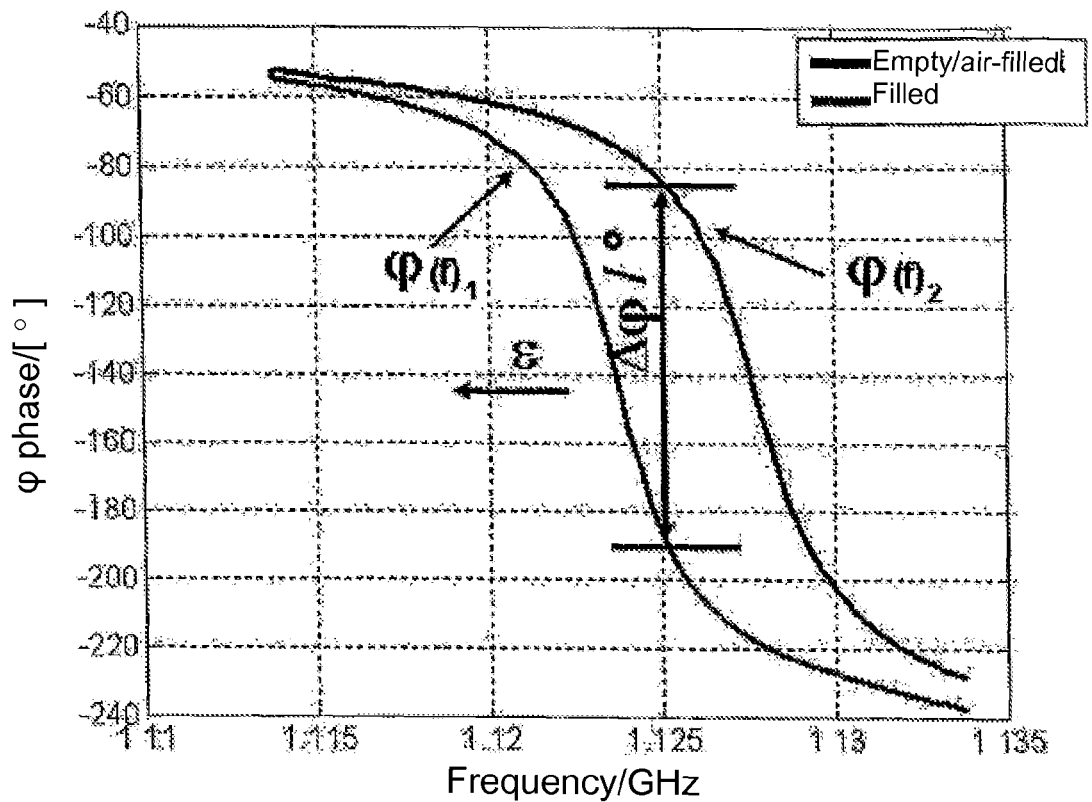

FIG. 3 shows a diagram of the absolute value of a signal $S_{21}$ from a filled and an empty/air-filled line resonator according to FIGS. 1a) through 2. The function $S_{21}(f)_1$ indicates the signal curve for a line resonator filled with the medium 5, and $S_{21}(f)_2$ indicates the signal curve for an empty or air-filled line resonator according to FIGS. 1a), 1b), and 2. If a medium 5 having a dielectric constant $\in_r > 1$ flows through the measuring tube 3, or the measuring tube is filled with this medium 5, the resonance frequency $f_0$ is reduced in inverse proportion. The phase shift of the transmitted signal $S_{21}$, which is likewise correlated with $\in_r$, is illustrated in FIG. 4. At a suitable fixed frequency (in FIG. 4, at 1.125 GHz) a particularly strong contrast is noted in the phase difference $\Delta\phi$. The measured phase difference $\Delta\phi$ between function $\phi(f)_1$ for the line resonator filled with medium 5 and function $\phi(f)_2$ for the empty or air-filled line resonator thus allows conclusions to be drawn concerning the $\in_r$ of the medium 5. If the dielectric constant $\in_r$ of the medium 5 is known, conclusions may instead be drawn concerning the material distribution, i.e., the distribution of the medium 5 inside the tube 3.

The theoretical basis for the measurement method used is briefly described below.

Figure 5:
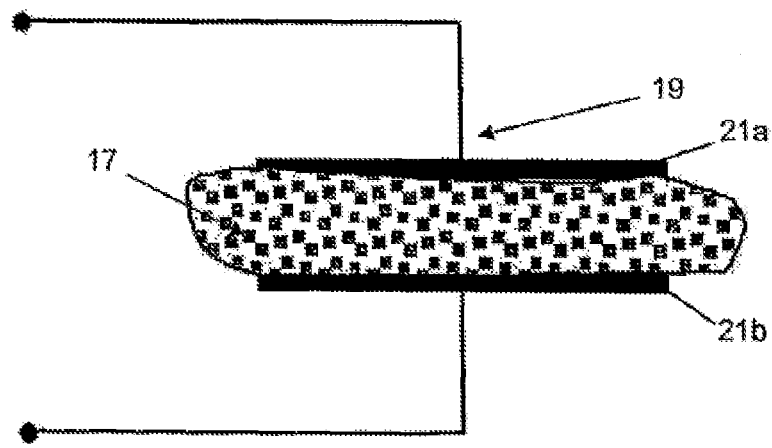

In principle, the relative permittivity or dielectricity $\in_r$ may be determined most easily by inserting a material sample 17 into a capacitor assembly 19 which, as illustrated in FIG. 5, basically comprises two oppositely situated capacitor plates 21a, 21b between which the material sample 17 is provided. The permittivity of the introduced material sample 17 may be directly determined from the relative change in capacitance ($\Delta C/C$) according to formula (1) when a reference capacitance $C_R$ has been previously measured for an empty or air-filled capacitor assembly 19 having a permittivity of $\in_r = 1$. By measuring the capacitance C of the capacitor assembly 19 filled with the material sample 17 to be investigated, the change in capacitance ($\Delta C/C = (C-C_R)/C$) may then be determined.

$$\varepsilon_r = \frac{1}{\varepsilon_0} \cdot \frac{\Delta C}{C} \quad (1)$$

For very small relative changes in capacitance ($\Delta C/C$), as the result of noise or other effects problems may arise in the evaluation of signals. In addition, it may no longer be possible to regard the capacitor assembly 19 together with the material sample 17 as a discrete component when the frequency at which the capacitance measurement is performed is too high. For this reason, high-frequency techniques must be used in order to allow meaningful evaluation.

In addition to the capacitive portions of a line resonator, the inductivity L also influences the properties of the line resonator. The inductivity is greatly influenced by the (relative) permeability $\mu_r$ of a material introduced into the line resonator.

Figure 6:
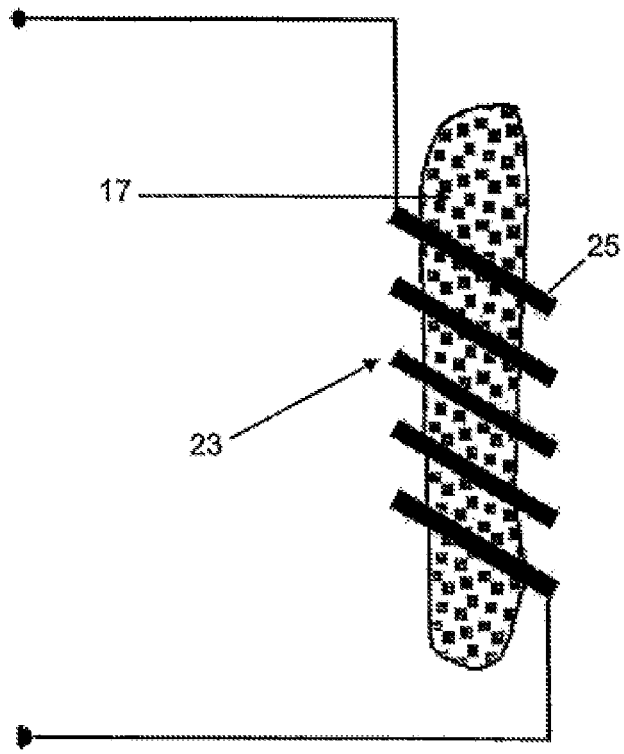

As illustrated in FIG. 6, the permeability $\mu_r$ of the material may be determined by introducing the material sample 17 into a coil assembly 23 having windings 25, i.e., by use of the inductivity L. Analogously to the capacitor assembly 19, the permeability $\mu_r$ is determined by the relative change in inductivity ($\Delta L/L$) according to formula (2).

$$\mu_r = \frac{1}{\mu_0} \cdot \frac{\Delta L}{L} \quad (2)$$

To allow measurement of very small changes in permittivity ($\Delta \in_r$), using the capacitor assembly 19 from FIG. 5 a resonant circuit may be formed by adding an external coil assembly 23 shown in FIG. 6. The changes in the permittivity cause a change in the capacitance C according to formula (1), resulting in a shift in the resonance frequency f. If the measurement is performed at a constant frequency $f_0$, detuning of the resonance frequency results in evaluatable information in the form of the modified phase angle $\phi$ of the transmitted signal.

Figure 7:
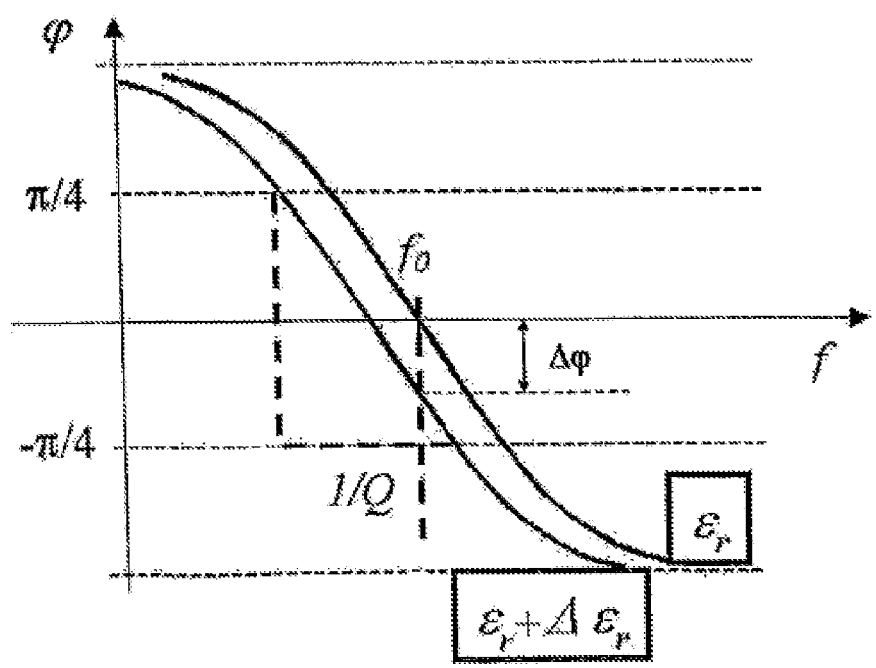

In a resonator having such a design, the following approximation is valid for the change in phase (angle) $\Delta\phi$, as graphically illustrated in FIG. 7:

$$\Delta\varphi = \frac{\pi/2}{1/Q} \cdot \frac{\Delta f}{f_0} = 180° \cdot Q \cdot \frac{\Delta \varepsilon_r}{2} \quad (3)$$

where Q is the quality of the resonator, and it is assumed that $\Delta \in_r / \in_r \ll 1$. The empty or air-filled capacitance measuring apparatus 19 is filled with a material sample 17 having permittivity $\in_r$. For air, $\in_r$ is approximately 1. The slope of $\phi(f)$ at $f_0$ is $$\frac{\pi/2}{1/Q} \quad (4)$$

The quality Q of an LC oscillating circuit which is connected to an electronic evaluation system or measuring circuit, for example a network analyzer 13 (see FIG. 1b)) having internal resistance $R_0$, is obtained from formula (5):

$$Q = \frac{\sqrt{L/C}}{R_0} \quad (5)$$

It is assumed that the external coil assembly 23 experiences no losses. If the losses in the coil assembly 23 are too high, the quality of the resonant circuit, and therefore also the measurement variable $\Delta\phi$, are reduced.

In an analogous manner the LC oscillating circuit may likewise be detuned by varying the inductivity. The capacitor assembly 19 is replaced by a capacitor with fixed capacitance and the coil is replaced by a measuring coil assembly 23; i.e., the coil assembly 23 is suitable for at least temporarily accommodating a material sample 17.

For the phase change, the following approximation from the graphical illustration in FIG. 7 results:

$$\Delta \varphi = 180° \cdot Q \cdot \frac{1}{2 \cdot \Delta \mu_r} \quad (6)$$

For measuring the permittivity, besides discrete capacitor assemblies 19, which optionally are operated using an external coil assembly 23 in resonance, line resonators may also be used. Such a line resonator 27 is schematically shown in FIG. 8. The line resonator 27 essentially comprises two substantially parallel lines 29a, 29b. These lines may be designed, for example, as coaxial lines wherein, for example, line 29a may be an inner conductor [sic; line] and line 29b may be an outer line coaxially surrounding the inner line. Lines 29a, 29b are short-circuited at a first end 31a, and at a second end 31b are connected to a measuring circuit having an internal resistance $R_0$. Harmonic electromagnetic oscillations may be produced inside the line resonator 27. A good approximation of the quality of the line resonator 27 is represented by $$Q \approx \frac{1}{\sqrt{2}} \cdot \left( \frac{R_0}{Z_L} + \frac{Z_L}{R_0} \right) \cdot n. \quad (7)$$

$Z_L$ is the characteristic impedance of the line resonator 27, and n is the order of the oscillations produced in the line resonator 27. Thus, the line resonator 27 has a length $n*\lambda/2$, where $\lambda$ is the wavelength of the oscillation produced in the line resonator. It follows from formula (3) that a maximum output signal $\Delta\phi$ may be achieved by means of the following measures:

1. Operating the resonator at a harmonic oscillation having the highest possible order n, thereby increasing the resonance frequency in conventional resonators.

2. Reducing the load on the resonator, thus increasing the quality Q. For high-frequency systems, the reference impedance is generally 50$\Omega$. The load on the resonator may be reduced, for example, by means of a weak capacitive or inductive coupling.

3. Optimizing the characteristic impedance $Z_L$.

When a line resonator is provided as illustrated in FIGS. 1a), 1b), and 2, there is a conflict of goals between the demand for minimizing space requirements and simultaneously maximizing the quality Q. Thus, for example, in order to increase the quality Q of the resonator it would be desirable to operate a line at a frequency as low as possible, at a resonance having a high order n. However, reducing the frequency can be achieved only by increasing the dimensions of the resonator, which is in conflict with the desire for the smallest possible size of the device.

In addition, the resonator measuring systems known from the prior art require intensive adjustment before performing a measurement. Thus, directional couplers which are used for coupling the microwave signal in must be matched to an existing tube diameter of a waveguide. Furthermore, in such measuring systems the measurement quality is degraded by reflections outside the measuring path. Lastly, the desired high operating frequencies, particularly at high GHz ranges, result in increased costs for the microwave source as well as the necessary electronic evaluation system, which rise with increasing operating frequency.

Furthermore, the use of generic devices in the form of LHRH lines as antenna elements is known from the articles "Applications of Infinite Wavelenghts Phenomenon," Proceedings of the 36th European Conference, September 2006, XP 31005725 A, and "Composite Right/Left-Handed transmission Lines Based on Conductor-Baded Coplanar Strips," IEICE Trans. Electron., Vol. E89-C, No. 9, September 2006, XP 1542402 A.

The object of the present invention is to refine the generic device in such a way that the disadvantages of the prior art are overcome, and in particular to provide a device which allows a parameter of a medium to be determined with comparatively high sensitivity and resolution limits, and which at the same time is not extremely complex and is very compact, which allows a velocity and/or a mass flow of a medium through a measuring path to be determined, and which may be operated at comparatively low signal frequencies and is therefore economical. A further object is to provide a method, which is an improvement over the prior art, for determining at least one parameter of a medium.

The object relating to the device is achieved by the fact that the device is provided for determining at least one parameter of a medium, and is characterized by means for introducing the medium into the measuring path in such a way that the electrical properties of the capacitive element may be modified by the medium, and by using the measuring path an electromagnetic field may be coupled into and/or coupled out of the medium in places by introducing the electrical and/or electromagnetic signal into the measuring path, and the device for determining the parameter of the medium has an evaluation device for analyzing an output signal of the measuring path.

It may be provided in particular that a dimension, particularly a dimension along the measuring path, of at least one elementary cell, preferably of all elementary cells, at least in places is smaller than a wavelength of the electrical and/or electromagnetic signal and/or of the electromagnetic field.

It may be provided that the evaluation device is designed in such a way that as a parameter of the medium, at least a relative dielectric constant, a relative permeability constant, a type of medium, a density distribution and/or the density of the medium, a distribution of the medium in the measuring path, a velocity of the medium in the measuring path, a quantity flow and/or mass flow of the medium through the measuring path, and/or a phase state of the medium, such as liquid, solid, and/or gaseous, may be determined. Furthermore, the invention provides that the device is designed in such a way that as the medium, a fluid, in particular a liquid and/or gas, and/or solid, in particular powdered and/or granular, medium, and/or a medium comprising two phases, such as liquid-gaseous, liquid-solid, liquid-liquid, gaseous-solid, solid-solid, gaseous-gaseous, and/or liquid-gaseous-solid, may be introduced into the measuring path.

In the above-referenced embodiments the invention further provides that the medium is movable relative to the line system.

It is particularly preferred that the measuring path includes at least one conducting unit for conducting the medium, such as a tube, channel, and/or conveyor belt, whereby the line system may be situated, at least in places, in the region of the conducting unit, in particular on at least one surface thereof, in such a way that the electromagnetic field may be injected into the medium, at least in places.

For the above-referenced alternative, according to the invention it is preferred that the conducting unit has, at least in places, a circular, oval, elliptical, triangular, square, rectangular, and/or polygonal cross section and/or segments of these cross sections, such as a circular segment and/or ellipsoidal segment.

The two embodiments referenced above may be characterized in that the conducting unit, at least in places, includes a dielectric and diamagnetic material, in particular glass, a synthetic material such as plastic, ceramic, and/or an elastically and/or plastically deformable material.

Furthermore, the invention provides a device which is designed in such a way that the medium may be provided in the conducting unit and/or may be conducted by the conducting unit.

In this embodiment the invention provides a conveying unit, such as a pump unit which operates by hydraulic, pneumatic, magnetic, and/or gravitational means, via which the medium may be conducted through the conducting unit.

The device according to the invention may be further characterized in that the conducting unit is movable relative to the line system.

One advantageous embodiment of the invention further provides that the device is designed in such a way that as an electrical and/or electromagnetic signal, at least one high-frequency signal, in particular a microwave signal and/or millimeter-wave signal, may be introduced into the measuring path, and/or high-frequency electromagnetic radiation, in particular microwave radiation and/or millimeter-wave radiation, may be coupled into the medium.

In this embodiment the invention further provides that at least one output of the generator is connected to at least one input of the electrical path of the first elementary cell, preferably by means of at least one coaxial cable, wherein preferably at least one conductor for the coaxial cable, in particular at least one external conductor, is connected, at least indirectly, to the electrical ground.

Preferred embodiments of the invention provide that the line system includes at least one capacitive element comprising at least one first charging element and at least one second charging element, such as in the form of at least one pair of capacitor plates, wherein preferably the first and/or the second charging element, in particular at least one of the capacitor plates, may be situated, at least in places, on at least one side facing away from the medium, in particular on a surface of the conducting unit which preferably is curved and/or nonplanar, at least in places, and/or include(s), at least in places, an electrically conductive material such as copper, metal, steel, silver, at least one semiconductor material, and/or at least one polymeric material.

The invention further provides that the device is designed in such a way that the electromagnetic field is generated between the first and the second charging element, wherein in particular the electromagnetic field is generated between charging elements of different elementary cells.

In particular for the two embodiments referenced above, the invention provides a device which is characterized by a design in which the medium is situated between the first and the second charging element, and preferably the first and second charging elements are situated on opposite sides of the conveying unit.

It is particularly preferred that the first and second charging elements are situated, at least in places, opposite from one another, in particular in a parallel and/or plane-parallel manner.

Preferred embodiments of the invention provide that the first and second charging elements are offset relative to another, in particular along at least one longitudinal axis of the conducting unit.

The invention further provides a device which is designed in such a way that the line system includes at least one third elementary cell inserted between the first and second elementary cells, wherein the capacitive element of the third elementary cell is situated in the electrical path of the third elementary cell, at least one inductive element connects the electrical path of the third elementary cell to the electrical ground, and/or at least one input of the electrical path of the third elementary cell is connected to at least one output of the electrical path of the first elementary cell in place of the second elementary cell, and/or at least one output of the electrical path of the third elementary cell is connected to at least one input of the electrical path of the second elementary cell in place of the first elementary cell.

For this device it may be provided that the device includes a plurality of third elementary cells, wherein in particular an output of the electrical path of a first third elementary cell is connected to an input of the electrical path of at least one second third elementary cell.

It is particularly preferred that at least two first, second, and/or third elementary cells and/or combinations of these elementary cells are periodically oriented toward one another.

In this embodiment it is further preferred that at least one input of the evaluation device is connected to at least one output of the electrical path of the second elementary cell, and/or to at least one output of the generator, in particular by means of at least one coaxial cable, wherein preferably at least one conductor for the coaxial cable, in particular at least one external conductor, is connected, at least indirectly, to the electrical ground.

The invention further provides a device which is characterized in that at least one input of the evaluation device is connected to the input of the electrical path of the first elementary cell, in particular by means of at least one coaxial cable, wherein preferably at least one conductor for the coaxial cable, in particular at least one external conductor, is connected, at least indirectly, to the electrical ground, and/or the output of the electrical path of the second elementary cell is connected to the electrical ground.

It is further preferred that the evaluation device compares an electrical and/or electromagnetic input signal which is present at at least one output of the generator and/or at at least one input and/or one output of the electrical path of an elementary cell, in particular the input of the electrical path of the first elementary cell, with an electrical and/or electromagnetic output signal which is present at an output and/or at an input of at least one elementary cell, in particular the output of the electrical path of the second elementary cell and/or the input of the electrical path of the first elementary cell, after passing at least partially through the line system.

For this device the invention further provides that the evaluation device is designed in such a way that at least one amplitude, in particular an absolute value, at least one phase, and/or at least one phase angle, of the at least one electrical and/or electromagnetic input signal and/or of the at least one electrical and/or electromagnetic output signal may be detected.

For the device, the invention further provides that the evaluation device is designed in such a way that at least one phase change, in particular at least one phase angle change, preferably between the voltage and current, between the at least one electrical and/or electromagnetic input signal and/or the at least one electrical and/or electromagnetic output signal may be detected.

A further alternative embodiment of the invention is characterized in that the evaluation device includes at least one processor unit, such as a microprocessor, and/or at least one visual and/or acoustic output device, in particular for outputting the given parameter of the medium.

It may also be provided in particular that the evaluation device includes at least one first evaluation unit for determining a first parameter of the medium, such as the density of the medium, and at least one second evaluation unit for determining a second parameter of the medium, such as a velocity of the medium.

For this embodiment the invention provides that the device is characterized by at least one third evaluation unit included in the evaluation device for determining a third parameter of the medium, such as the quantity flow and/or mass flow of the medium through the measuring path, in particular based on the first and the second parameter of the medium.

For the two embodiments referenced above, also provided is at least one transformation unit included in the evaluation device, wherein by means of the transformation unit the electrical and/or electromagnetic output signal of the measuring path and/or at least one comparative signal determined by a comparison of the electrical and/or electromagnetic input signal of the measuring path which in particular is adjusted, for example phase-shifted, with the electrical and/or electromagnetic output signal of the measuring path, may be transformed, in particular by Fourier transformation, wherein in particular the first evaluation unit and/or the second evaluation unit is/are operatively connected to the transformation unit, and preferably the first evaluation unit and/or the second evaluation unit may be connected to the measuring path via the transformation unit.

The invention further provides that at least one input of an elementary cell and at least one output of at least one additional elementary cell are directly connected to one another.

It is further preferred that the input signal may be injected via at least one input and/or at least one output of at least one elementary cell, and the output signal may be extracted at the same input and/or output.

It is further preferred that at least one inductive element of at least one first, at least one second, and/or at least one third elementary cell includes at least one conductor, such as a wire, and/or at least one coil.

Lastly, for the device the invention provides that the elementary cells are associated with the conducting unit along at least one longitudinal direction and/or at least along one radial direction.

The object relating to the method is achieved by a method for determining at least one parameter of a medium, in particular by using a device according to the invention, wherein the parameter is determined on the basis of at least one change in at least one electrical property of a capacitive element of at least one measuring path which interacts with the medium, wherein within the measuring path at least one zeroth-order and/or negative-order harmonic electromagnetic oscillation is selected or generated by supplying a high-frequency input signal to the measuring path, and at least one amplitude, at least one phase angle change, and/or at least one phase angle of the oscillation after passing through the measuring path is determined, and the parameter of the medium is determined based on the amplitude and/or the phase angle.

A method according to the invention may be further improved by supplying the input signal to a line system comprising at least one series connection of at least two elementary cells, each having at least one capacitive element and at least one inductive element, wherein the capacitive elements are connected in series, and the inductive elements connect the capacitive elements to an electrical ground.

For the method, the invention further provides that an absolute value of an amplitude and/or a phase angle between the current and voltage of the oscillation is determined, and/or the parameter of the medium is determined by comparison, in particular time-based comparison, of input and output signals of the measuring path which in particular are adjusted, for example phase-shifted, and/or by comparison, in particular time-based comparison, of at least one electromagnetic oscillation without influence of the medium on the measuring path, and at least one electromagnetic oscillation with influence of the medium on the measuring path.

The invention further provides that at least one dust-like material, in particular pneumatically conveyed, preferably comprising at least one organic material such as carbon, at least one inorganic material such as glass, plastic, and/or ceramic, at least one liquid such as oil, water, at least one bodily fluid such as blood and/or saliva, and/or at least one bulk material is used as medium.

The invention provides in particular that the output signal of the measuring path and/or a comparative signal obtained by comparing the input signal and the output signal of the measuring path, in particular a signal which represents a phase difference, is transformed into at least one transformed signal, in particular by Fourier transformation.

It is further preferred that, by use of at least one first evaluation unit, at least one first parameter of the medium is determined on the basis of the output signal of the measuring path, the input signal of the measuring path, the comparative signal, and/or the transformed signal.

Alternatively or additionally it may be provided that, by use of at least one second evaluation unit, at least one second parameter of the medium is determined on the basis of the output signal of the measuring path, the input signal of the measuring path, the comparative signal, and/or the transformed signal.

In the two embodiments referenced above it is particularly preferred that by use of the first evaluation unit and/or the second evaluation unit the output signal of the measuring path, the input signal of the measuring path, the comparative signal, and/or the transformed signal is filtered, preferably using at least one first filter unit, such as a low-pass filter unit, included in the first evaluation unit, and/or using at least one filter unit, such as a high-pass filter unit, included in the second evaluation unit.

The method according to the invention may be characterized in that the first parameter is ascertained by determining at least one average value of the output signal of the measuring path, the input signal of the measuring path, the comparative signal, the transformed signal, the filtered output signal of the measuring path, the filtered input signal of the measuring path, the filtered comparative signal, and/or the filtered transformed signal, and/or the second parameter is ascertained by determining at least one maximum value, in particular a maximum point of a function and/or a magnitude of a maximum value, and/or a number of maximum values, in particular by means of at least one time-based derivation and/or a derivation according to a frequency, of the output signal of the measuring path, the input signal of the measuring path, the comparative signal, the transformed signal, the filtered output signal of the measuring path, the filtered input signal of the measuring path, the filtered comparative signal, and/or the filtered transformed signal.

The invention further provides that by use of at least one third evaluation unit at least one third parameter of the medium is determined on the basis of the first parameter and the second parameter, wherein the third parameter is preferably determined by multiplying and/or adding the first and second parameters.

Lastly, the invention provides that as a parameter of the medium, in particular as a first parameter, second parameter, and/or third parameter, a relative dielectric constant, a relative permeability constant, a type of medium, a density distribution and/or the density of the medium, a distribution of the medium in the measuring path, a velocity of the medium in the measuring path, a quantity flow and/or mass flow of the medium through the measuring path, and/or a phase state of the medium, such as liquid, solid, and/or gaseous, is determined.

The invention is based on the unexpected finding that the determination of a parameter of a medium, for example a material density determination of a medium moving through a tube, is possible by using so-called left-handed structures which are mounted as electrically conductive structures in the region of a measuring path, in particular around a nonelectrically conductive section of conveying tube, to form a line system. By use of this system a high-frequency signal, in particular a microwave signal, may be introduced into the measuring path, for example the conveying tube, orthogonally with respect to the medium, in particular orthogonally with respect to the direction of propagation of the medium. When several of these conductive structures are mounted so as to be distributed on the conveying tube in the direction of propagation, by suitable connection of the capacitors thus produced a sensor based on a line resonator may be formed which in comparison to conventional material density sensors is very sensitive to the material density. Furthermore, by use of a single sensor the device according to the invention and the method according to the invention also allow the velocity of the medium through the measuring path to be determined at the same time, which permits the quantitative determination of a mass flow of the medium through the measuring path.

In addition, the conflict of goals, known from the prior art, between maximizing the quality and minimizing the space requirement, or in other words, reducing the geometric dimensions while simultaneously increasing the quality of a conventional device, i.e., a conventional resonator, is resolved by using such inverse lines or LH structures. Inverse lines have the following favorable characteristics:

1. The resonance frequency of the harmonic, i.e., of oscillations under resonance conditions, is below the frequency of the fundamental component. As a result, the dimensions of a resonator which is operated at a harmonic are not increased, thus allowing lower-frequency signals to be used, which lowers costs without sacrificing accuracy of the measurement.

2. The characteristic wave impedance $Z_L$ may be synthetically set in wide ranges as the result of using discrete components.

3. The same as for all resonators, the resonator quality may be further improved by reducing the external load.

The device according to the invention and the method according to the invention make use of the change in multiple capacitors distributed in the longitudinal direction for detuning a line resonator, and are based on the concept of the metamaterial, i.e., a material having a negative propagation constant. By making use of the properties of the metamaterial, which allows an increase in the order of resonance of a line resonator by reducing the frequency, a line resonator may be obtained which has such high sensitivity at low frequencies and with small sensor dimensions.

As a result of the design of the device according to the invention, i.e., the line resonator according to the invention, which includes inverse or LH elementary cells, very high sensitivity to changes in the density of a moving medium may be achieved by skillful choice of the resonance frequency. A system of multiple line resonators distributed over the circumference of the conveying element, such as a conveying tube with an associated increased sensitivity and resolution of differences in density, particularly in the tube cross section, is thus possible.

The sensitivity of a sensor from the prior art is increased by raising the order of the resonance mode, since for conventional line resonators having fixed dimensions the sensitivity increases with an increase in the resonator mode, and thus with the frequency. In contrast, for inverse line resonators as used in the device according to the invention, the resonance mode is increased by reducing the frequency. As a result, for the same frequency and the same sensitivity the required dimensions of the inverse line resonator are much smaller in comparison to a conventional line resonator. In addition, the design according to the invention increases the sensitivity of the sensor by several times for the same dimension and the same frequency.

In the following description it is noted that the material/medium to be investigated may be composed of a fluid, in particular in gaseous or liquid form, or solid, in particular powdered form, or may be composed of at least two phases, such as gas/solid, gas/liquid, or solid/liquid. For example, solid materials or media may be pneumatically conveyed.

Figure 2:
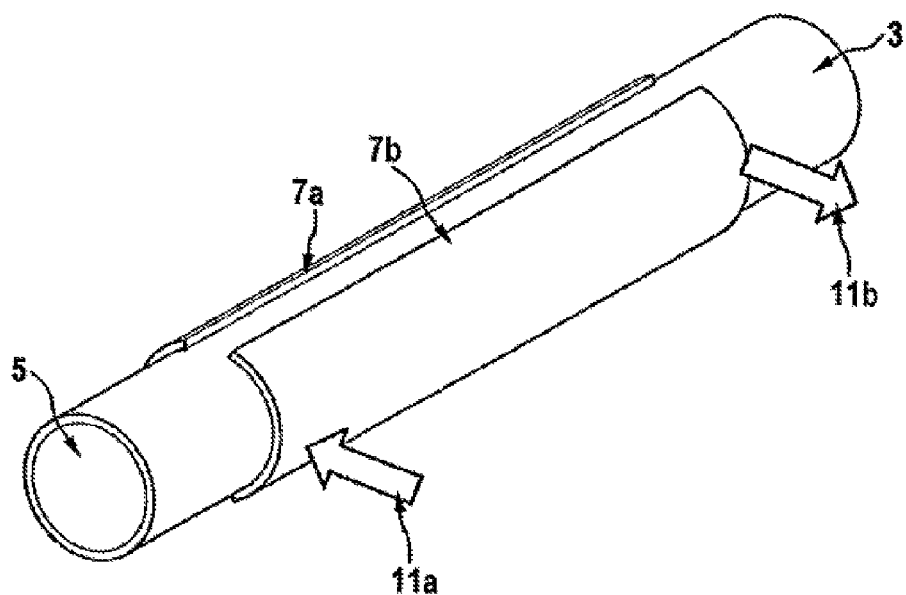
Figure 10A:
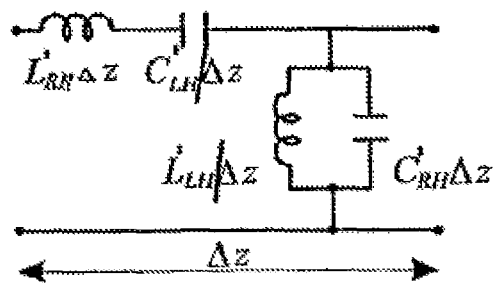
Figure 10B:
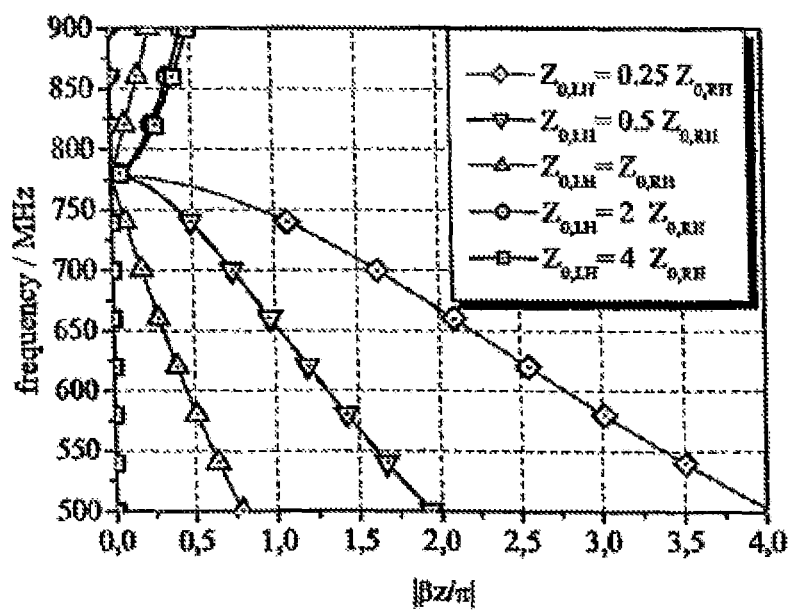
Figure 11:
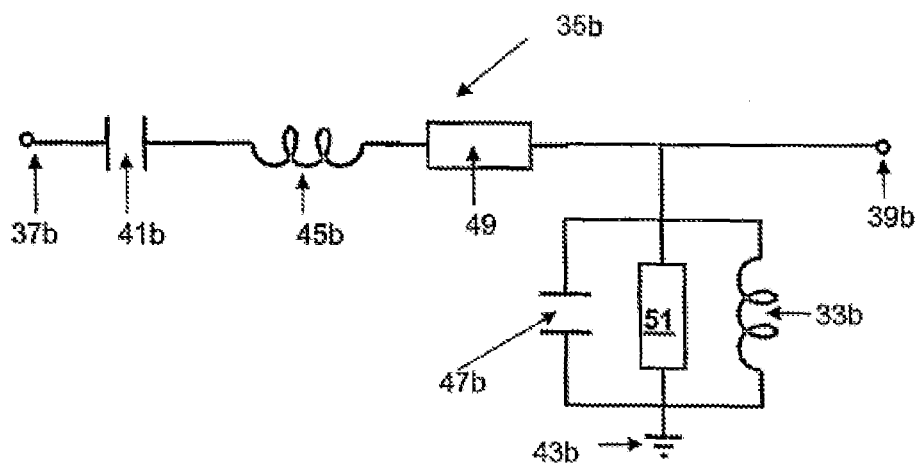
Figure 12:
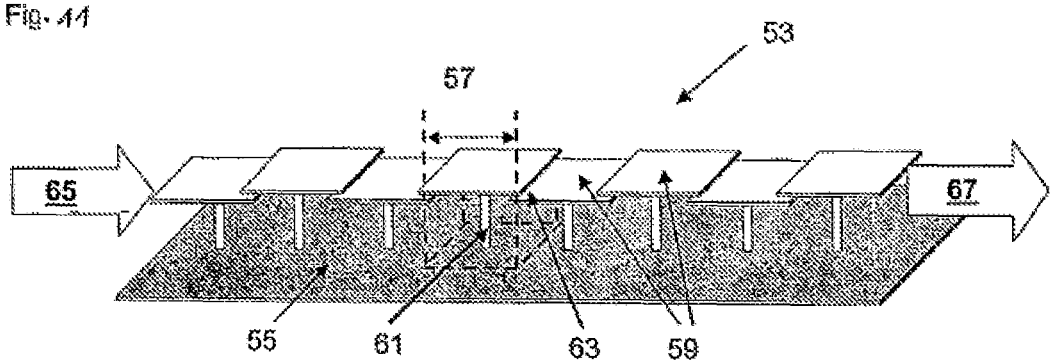
Figures 13A, 13B:
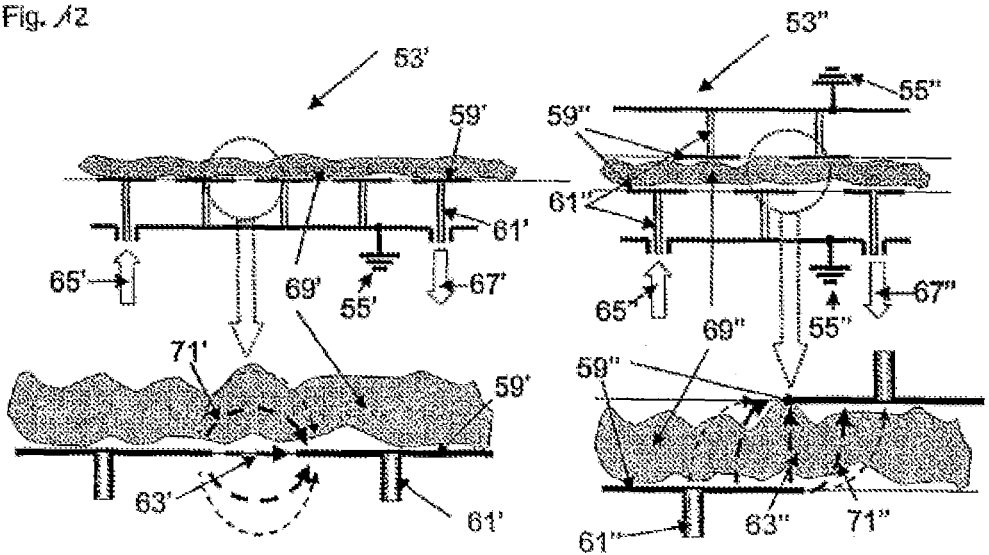
Figure 16:
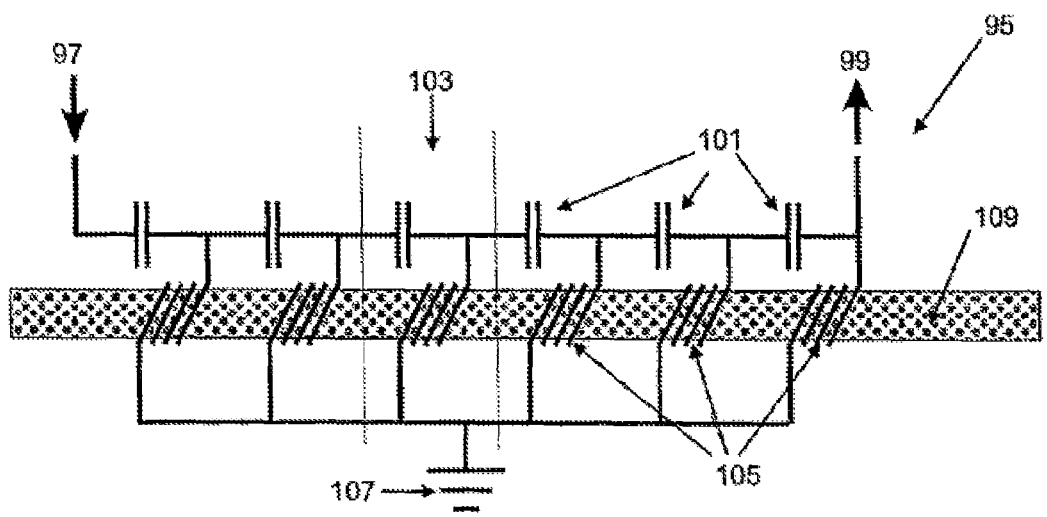
Figure 17:
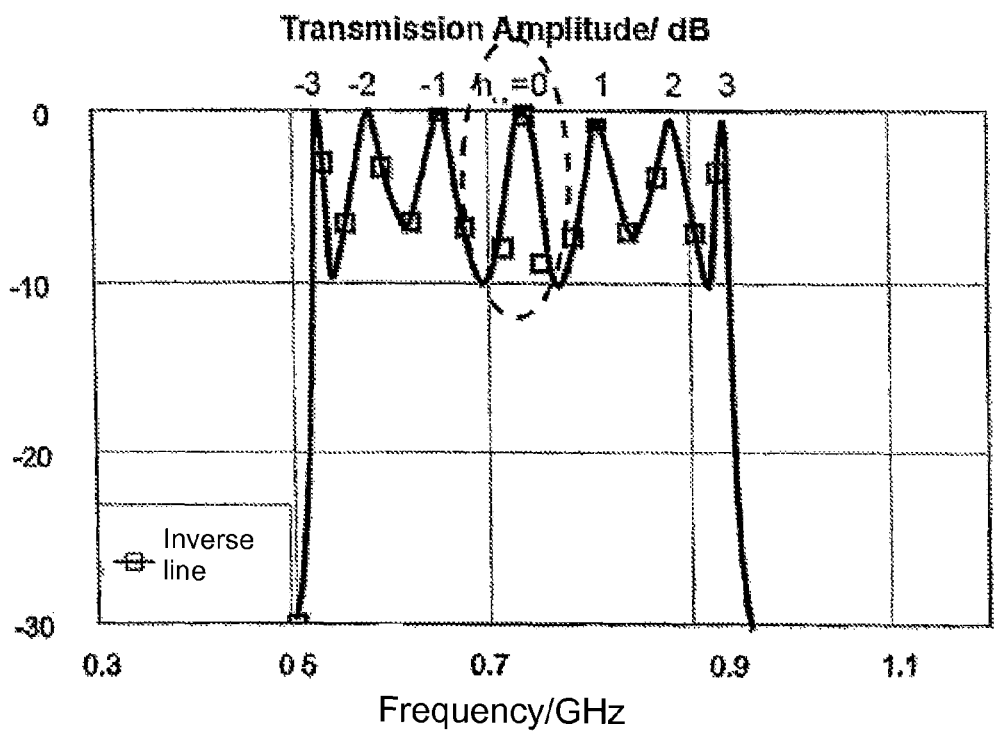
Figure 18:
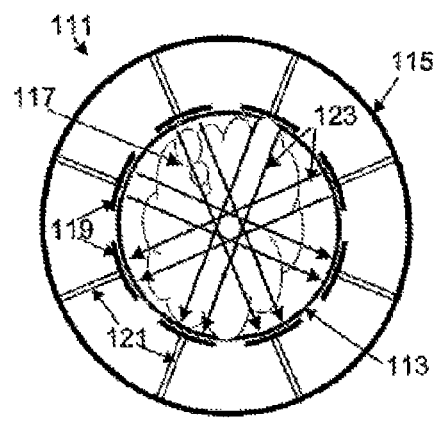
Figure 18:
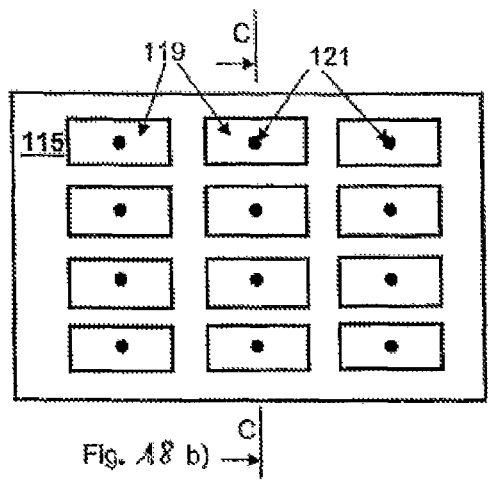
Figure 19:
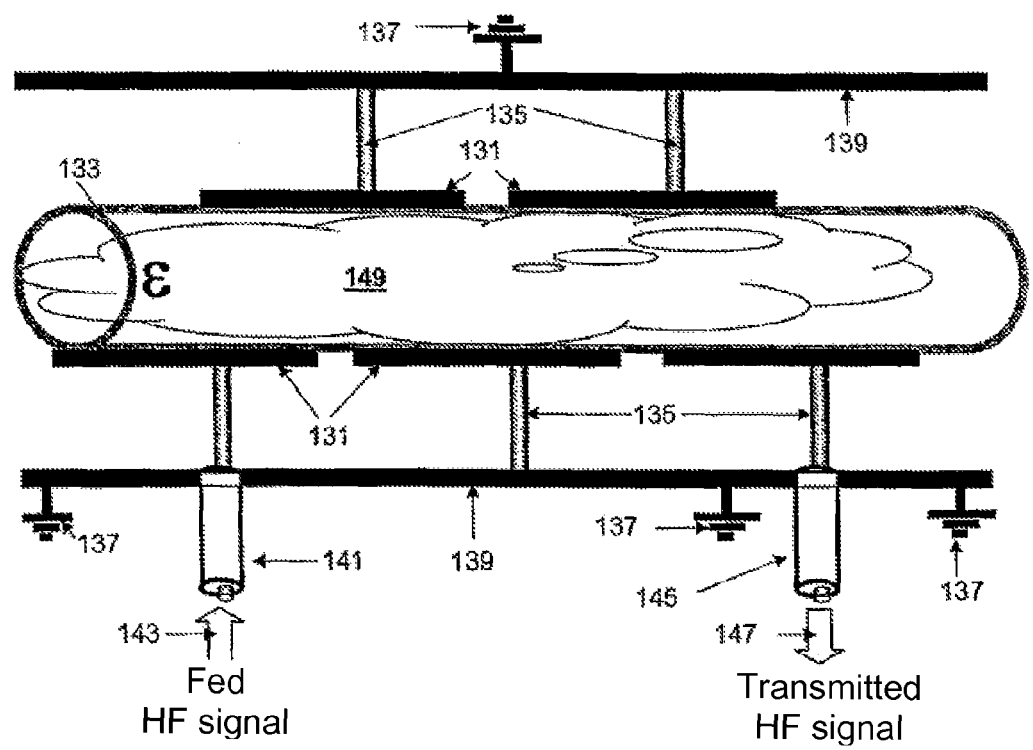
Figure 20:
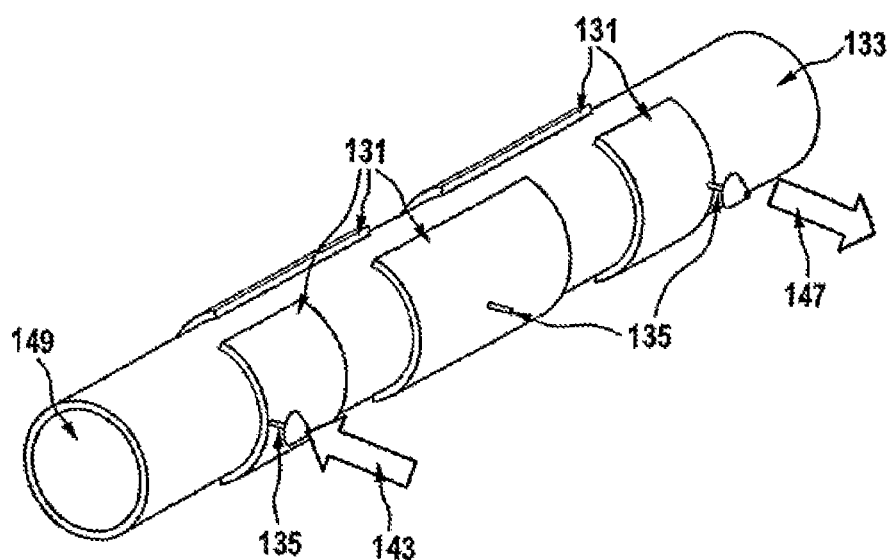
Figure 24:
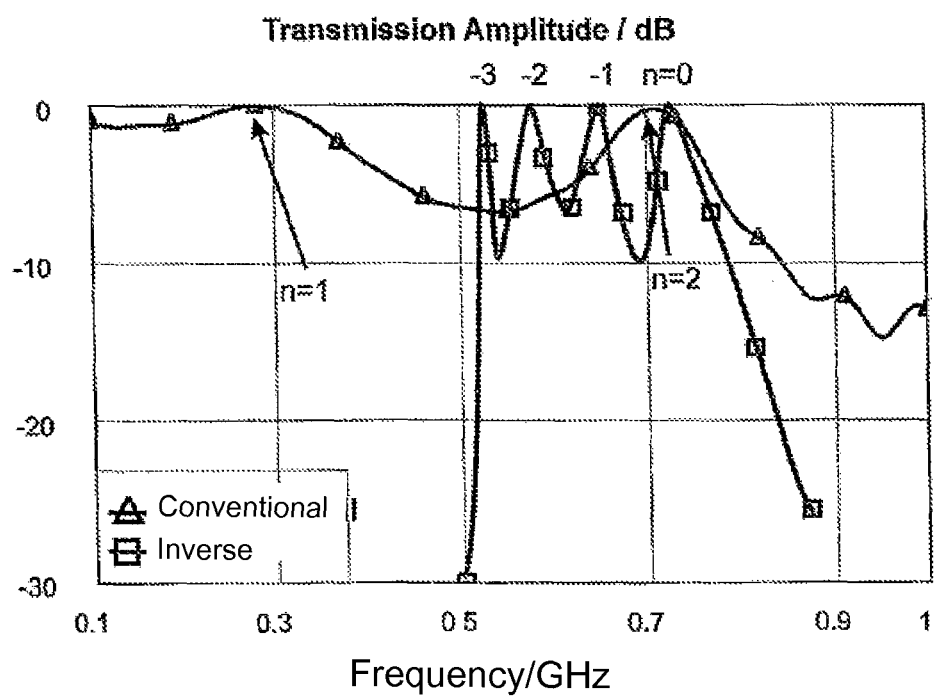
Figure 22:
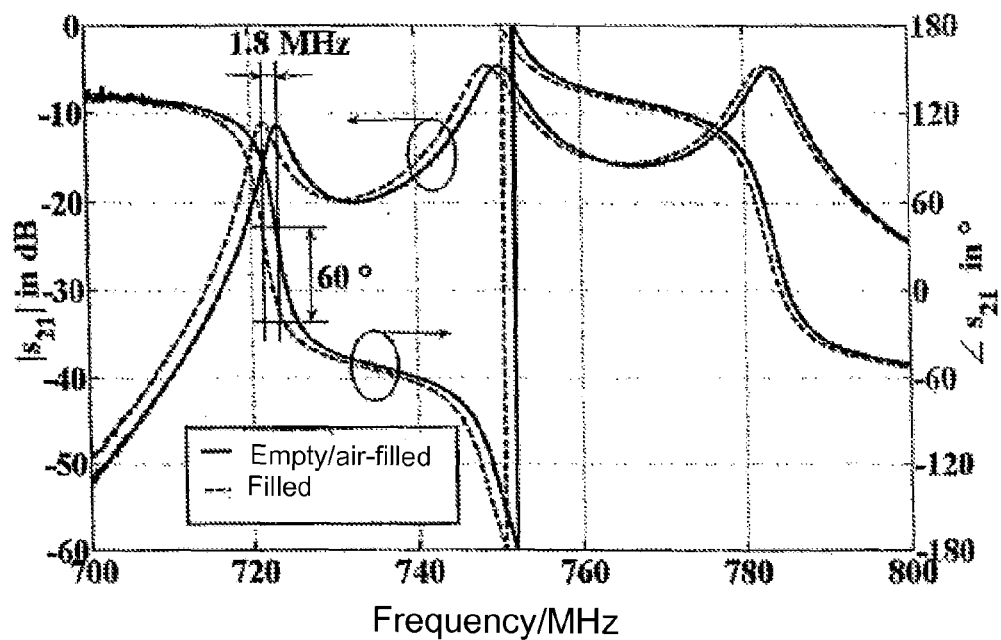
Figure 23:
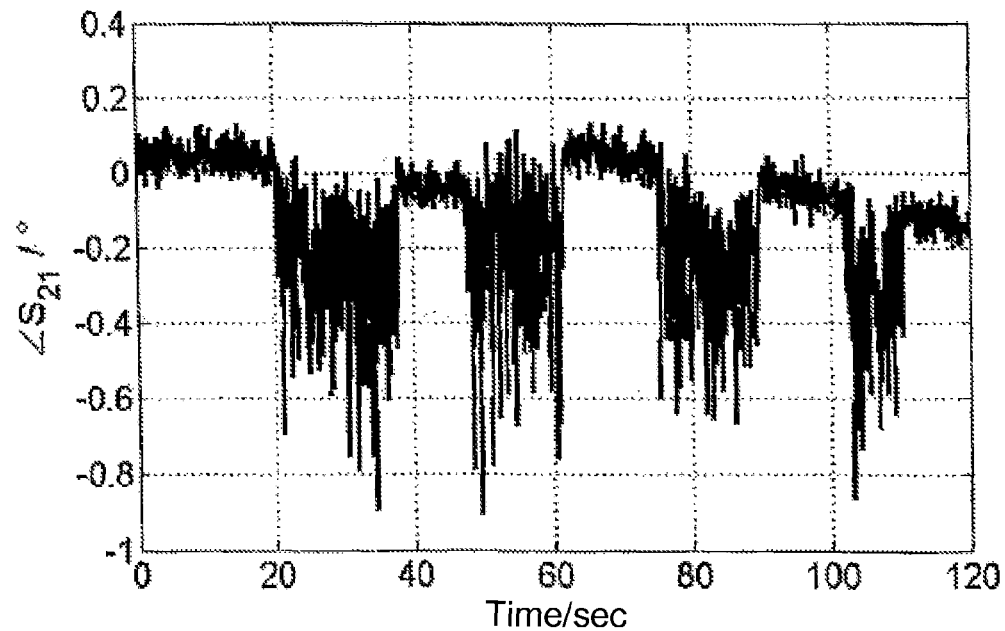
Figure 24:
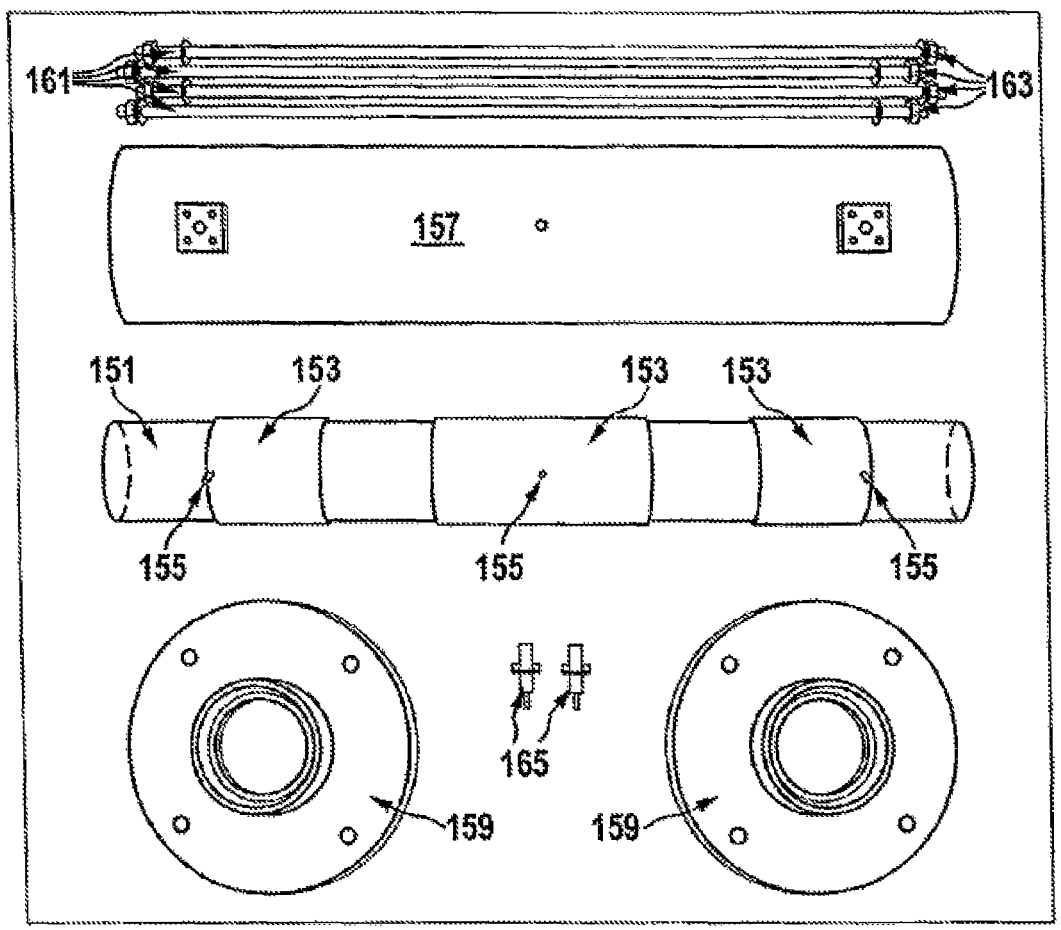
Figure 25:
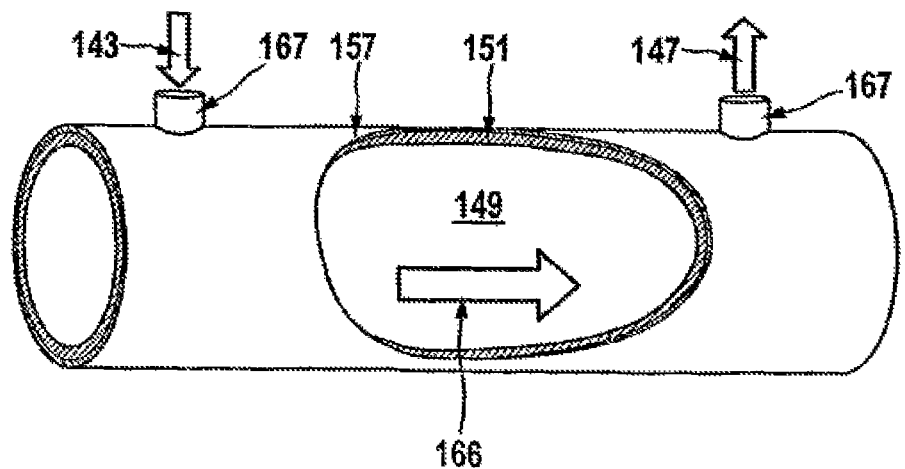
Figures 26A, 26B:
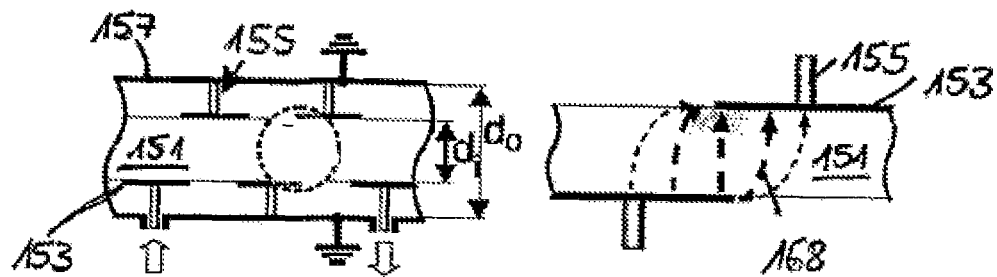
Figure 27:
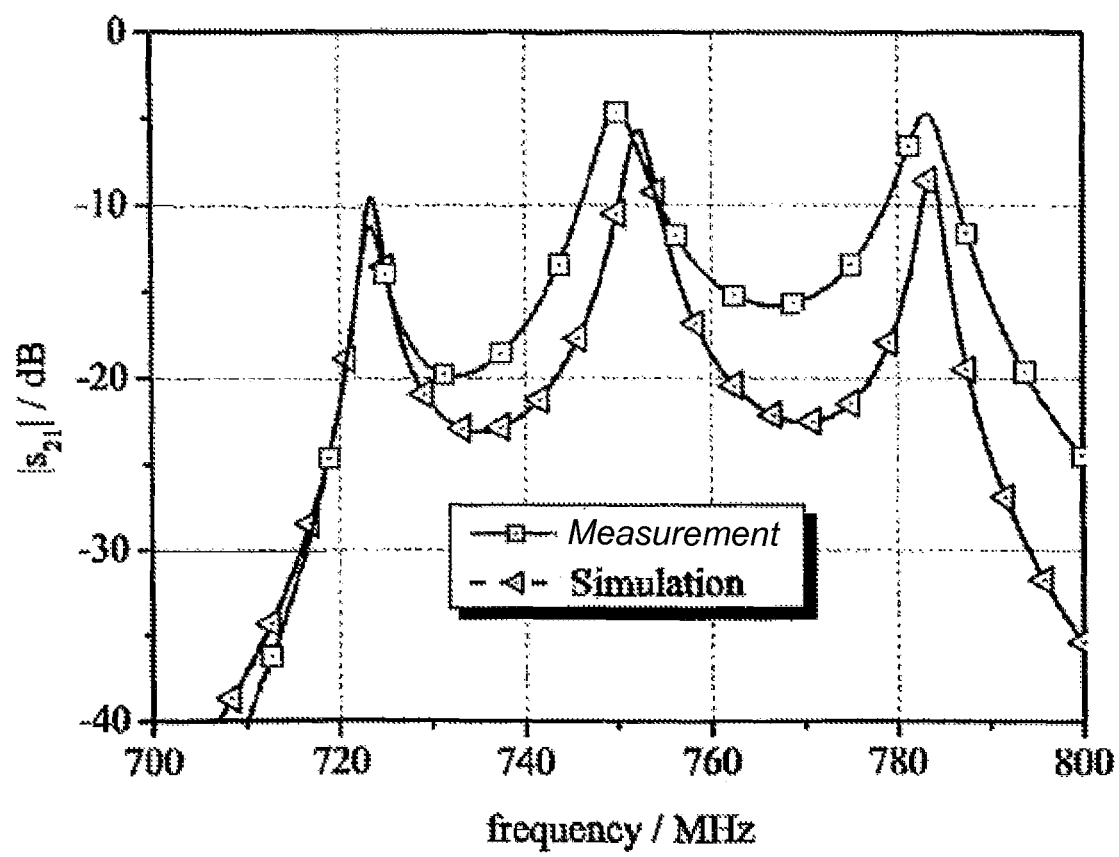
Figure 28:
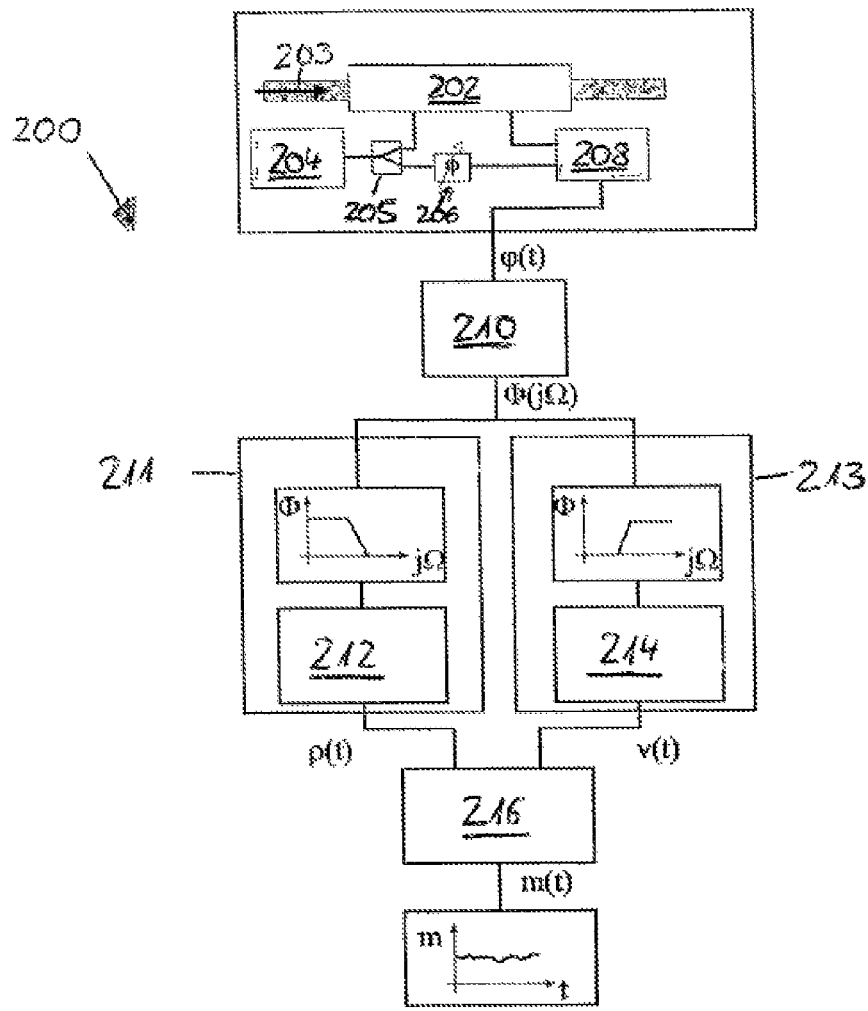
Figures 29A, 29B:
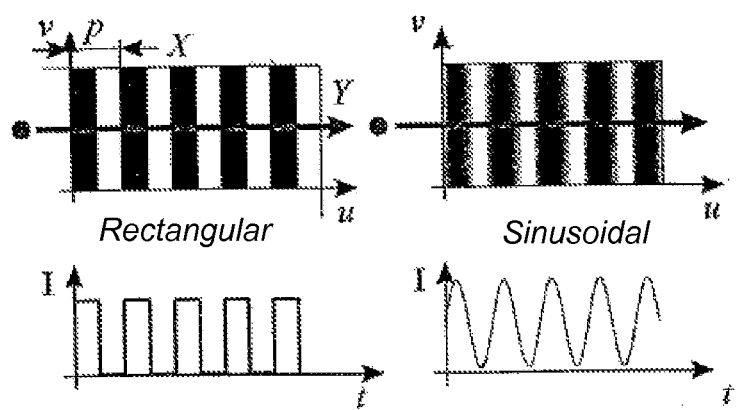
Figure 30A:
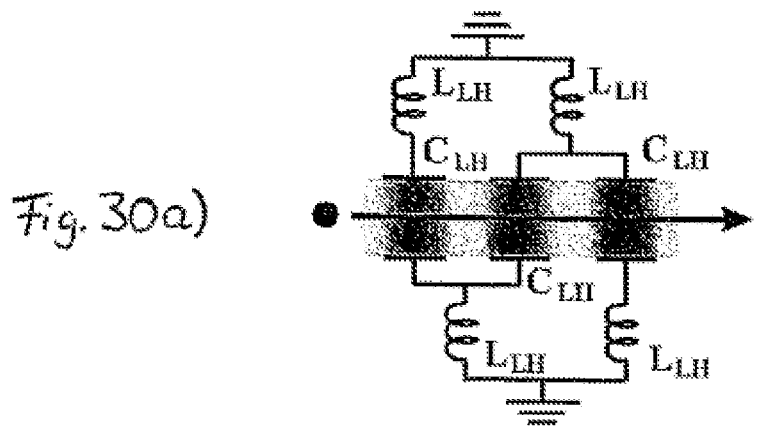
Figure 30B:
Figure 31:
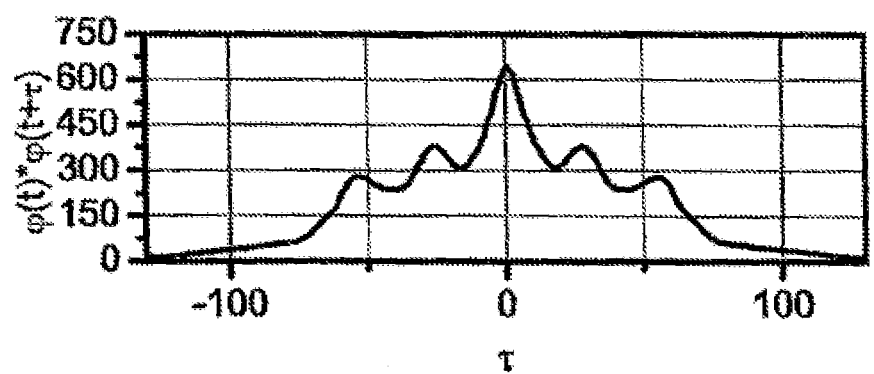

Exemplary embodiments of the invention are explained below with reference to the figures previously mentioned, as well as additional figures. Further features and advantages of the invention result from the following description, and the exemplary embodiments of a device according to the invention are explained by way of example with respect to several schematic drawings. The figures show the following:

FIG. 1: shows the design of a generic conventional RH resonator for determining the material density [in] a tube, a) as a longitudinal view of the entire structure from the side and b) as section A-A, perpendicular thereto, of the tube in direction B;

FIG. 2: shows a perspective view of a conventional RH resonator for determining the material distribution in a tube;

FIG. 3: shows the absolute signal from a conventional RH resonator from FIG. 1 as a function of the filling thereof with a material;

FIG. 4: shows the change in phase of an oscillating conventional RH resonator from FIG. 1 as a function of the filling thereof with a material;

FIG. 5: shows a capacitor filled with a dielectric material;

FIG. 6: shows a coil filled with a diamagnetic material;

FIG. 7: shows a diagram for estimating the phase change $\Delta\phi$ as a function of the resonator frequency f;

FIG. 8: shows a diagram of a line resonator;

FIG. 9: shows elementary cells for (a) a conventional (RH) line and (b) an inverse (LH) line;

FIG. 10a): shows an equivalent circuit diagram for a low-loss composite right-handed/left-handed transmission line (CRLH-TL);

FIG. 10b): shows dispersion diagrams for CRLH-TL unit cells having different RH and LH impedances;

FIG. 11: shows a further elementary cell for an RHLH line;

FIG. 12: shows the implementation diagram for an inverse line;

FIG. 13a) and FIG. 13b): show possible configurations for implementing an inverse line resonator for measuring the permittivity of materials;

FIG. 14: shows a variation in the geometric configuration for implementing a line resonator having periodic reactances; (cylindrically) conforming structure short-circuited at one end (one-port measurement);

FIG. 15a) and FIG. 15b): show further variations in the geometric configuration for implementing a line resonator having periodic reactances, in this case having (a) a planar and (b) a compact planar structure (two-port measurement in each case);

FIG. 16: shows one possible configuration for determining the permeability of solid or moving media;

FIG. 17: shows the transmission characteristics of a balanced RHLH line;

FIG. 18a and FIG. 18b: show the possible configuration of four line resonators on a dielectric tube: a) in the sectional plane transverse to the direction of propagation of the medium and b) along the direction of propagation, the cylinder shell being illustrated as a surface;

FIG. 19: shows the design of an inverse LH resonator according to the invention for determining the material distribution of a tube as a longitudinal section of the entire structure, from the side;

FIG. 20: shows a perspective view of an inverse LH resonator according to the invention for determining the material distribution of a tube;

FIG. 21: shows various absolute signals from a conventional RH resonator from FIG. 1 and from an inverse RHLH resonator according to the invention from FIG. 18;

FIG. 22: shows the signals from an inverse LH resonator according to the invention, one unfilled and one filled with Styropor ($\in_r$=1.024);

FIG. 23: shows the signal from an inverse LH resonator according to the invention for time-dependent, batchwise flow of millet through the sensor;

FIG. 24: shows the individual parts of a disassembled inverse LH resonator according to the invention;

FIG. 25: shows a perspective view of the design of an assembled inverse LH resonator according to the invention, with an oval cutout for viewing the processes inside the measuring path;

FIG. 26a) and FIG. 26b): show schematic cross-sectional views of various sections of the microstrip resonator of FIG. 25;

FIG. 27: shows a graphical comparison of values measured by the resonator of FIGS. 25 and 26a)/26b) to simulation data;

FIG. 28: shows a block diagram of a device according to the invention in the form of a sensor for determining a material density, a velocity, and a mass flow of a medium;

FIG. 29a) and FIG. 29b): show graphical illustrations of an output signal from a spatial filter upon passage of a particle with (a) rectangular and (b) sinusoidal transmittance;

FIGS. 30a and 30b: show graphical illustrations of a field distribution in a measuring path, in (a) a side view and (b) a top view; and FIG. 31: shows an autocorrelation of a high-pass filtered phase signal when a single object passes through the resonator according to the invention.

Inverse lines are implemented by the periodic positioning of reactive elements. The smallest unit of such a system is referred to as an elementary cell. FIG. 9 shows the electrical equivalent circuit diagram of the elementary cell of a conventional, i.e., RH line (FIG. 9a)) compared to an inverse, i.e., LH line (FIG. 9b)). As shown in FIG. 9a), the RH line elementary cell comprises an inductive component, for example in the form of a coil 33a, in a path 35a between connectors 37a and 39a, which represent an input and an output, respectively, of the elementary cell, the path 35a being connected to a ground 43a via a capacitive component, for example in the form of a capacitor 41a. In contrast, the LH line elementary cell according to FIG. 9b) comprises a capacitive component, for example in the form of a capacitor 41b, in a path 35b between connectors 37b and 39b, which represent an input and an output, respectively, of the elementary cell, the path 35b being connected to a ground 43b via an inductive component, for example in the form of a coil 33b.

The equivalent circuit diagrams illustrated in FIGS. 9a) and 9b), however, represent an ideal situation. However, as an inevitable result of the design, in particular of an inverse line having concentrated components, in addition to the components shown in FIG. 9b) stray capacitance and leakage inductance must be taken into account due to the feed lines, the design of the concentrated components (referred to as the package), and the physical configuration of the components.

An equivalent circuit diagram of a unit cell which also incorporates this effect is illustrated in FIG. 10a). $L'_{RH}\Delta z$, $L'_{LH}/\Delta z$, $C'_{LH}/\Delta z$, and $C'_{RH}\Delta z$ represent the respective right- and left-handed inductances and capacitances per unit length $\Delta z$. This circuit is also referred to as a loss-free combined or composite right-handed/left-handed transmission line (CRLH-TL) or CRLH line. The transmission constant is given by $$\gamma = \alpha + j\beta = \sqrt{Z'Y'}, \qquad (8)$$

where Z' and Y' are the impedance and the admittance, respectively, of the transmission line per unit length. These variables are defined by the following equations:

$$Y'(j\omega) = j\left(\omega L'_{RH} - \frac{1}{\omega C'_{LH}}\right), \qquad (9)$$

$$Z'(j\omega) = j\left(\omega C'_{RH} - \frac{1}{\omega L'_{LH}}\right).$$

For the phase constancy or dispersion relation $\beta$ (j$\omega$) the following expression applies:

$$\beta(j\omega) = \pm\sqrt{\omega^2 L'_{RH}C'_{RH} + \frac{1}{\omega^2 L'_{LH}C'_{LH}} - \left(\frac{L'_{RH}}{L'_{LH}} + \frac{C'_{RH}}{C'_{LH}}\right)}, \qquad (10)$$

where $\beta(j\omega)$ is a real value for the RH transmission band ($\beta$>0) and the LH transmission band ($\beta$<0). $\beta$ is an imaginary value outside the two transmission bands, resulting in a stop band.

A transmission line resonator as implemented in the device according to the invention by use of the line system is obtained when the transmission line is not perfectly matched at both ends. The RH and LH impedance is defined as $$Z_{0,RH/LH} = \sqrt{L'_{RH/LH}C'_{RH/LH}} \qquad (11)$$

FIG. 10b) shows dispersion diagrams of a composite right-handed/left-handed transmission line in the unbalanced state, i.e., $Z_{0,LH} \neq Z_{0,RH}$, and in the balanced state $Z_{0,LH} = Z_{0,RH}$. The increase in $\beta$ is inversely proportional to the quality or the Q factor of the resonance mode of the CRLH-TL resonator, i.e., of the line system in the empty or air-filled state. A flat dispersion curve, which is present for $Z_{0,LH} > Z_{0,RH}$, results in a high Q factor, i.e., high quality, and reduced mode distance between the resonance modes. The Q factor, i.e., the quality, of the resonator in the empty or air-filled state increases with the order of the resonance mode.

An unbalanced CRLH-TL resonator, which is observed in the higher-order modes in which $Z_{0,LH} > Z_{0,RH}$, allows sensitive permittivity sensors to be formed when the absolute changes in permittivity are small.

For a constant measurement frequency the phase shift, as described above by equation (3), may be estimated as a function of the change in permittivity according to the following equation:

$$\Delta\varphi = \frac{\pi}{2} \cdot Q \cdot \frac{\Delta\varepsilon_r}{2} \text{ for } \Delta\varepsilon_r/\varepsilon_{r,ref} \ll 1, \tag{12}$$

where Q is the Q factor, i.e., the quality in the filled state of the resonant circuit, and $\Delta\in_r$ is the difference $\in_{r_1meas} - \in_{r_1ref}$, i.e., the difference between the dielectric constant or permittivity measured using the medium and a reference dielectric constant or reference permittivity, for example in the empty or air-filled state of the resonator. A system sensitivity S may be defined as $$s = \frac{\Delta\varphi}{\Delta\varepsilon_r} = Q \cdot \frac{\pi}{4}. \tag{13}$$

A further equivalent circuit diagram of an elementary cell, supplemented in comparison to that illustrated in FIG. 10a), which also incorporates these effects is shown in FIG. 11. This elementary cell is referred to as an RHLH line, since it represents a combination of the elementary cells illustrated in FIGS. 9a) and 9b). In addition to the inductive 33b and the capacitive 41b portions of the LH elementary cell of FIG. 9b), also shown in the path 35b is a leakage inductance in the form of a coil 45b, and in the connection of the path 35b to the ground 43b, a stray capacitance in the form of a capacitor 47b. Also shown are two, in particular ohmic, equivalent resistors 49 and 51 which represent the in particular ohmic losses of the primarily inductive and the primarily capacitive region.

The structure acts as a right-handed (RH) or a left-handed (LH) line structure, depending on the frequency that is set. However, the invention relates in particular to the frequency range in which the structure acts as an inverse LH line structure, as well as the transition region of the RH line to the LH line, in particular regions in which the RH portions are essentially negligible.

The practical implementation of a measuring path comprising an LH line system 53 for determining a permittivity of a medium is illustrated in principle in FIG. 12. This is essentially the structure of a microstrip line, the substrate not being illustrated. The line system 53 includes a ground 55 on which a plurality of elementary cells 57, specifically, eight, are situated. Each of the elementary cells 57 includes respective inductors, in the form of wires 61, connected to the ground 55 and to upper metal platings or charging elements in the form of capacitor plates 59. The capacitor plates 59 form series capacitor plates which are separated from one another by gaps. Thereby capacitances 63 are formed between the capacitor plates 59. This results in a series connection of capacitive elements in a strip conductor which runs from a signal input 65 of a first elementary cell to a signal output 67 of a second elementary cell, six third elementary cells being situated between the first and second elementary cells.

FIGS. 13a) and 13b) illustrate two further alternative configurations of inverse line resonators or measuring paths for measuring the permittivity of materials 69', 69", which are used as the basis for explaining the formation of the inductive and capacitive elements. FIG. 13a) shows a line system 53' having a planar arrangement or configuration of the elementary cells, whereas FIG. 13b) shows a line system 53" having a three-dimensional configuration of the elementary cells in an inverse line resonator. The individual elements of line systems 53', 53", which correspond to those of line system 53 in FIG. 12, have the same reference numerals, except that they are followed by one or two apostrophes. FIGS. 13a and 13b each show a section of the line system 53' and 53", respectively, in an enlarged illustration. By means of the illustration of the electrical field lines 71' and 71", these sections clarify the regions in which capacitive elements are formed, so that the materials 69' and 69" result in changes in capacitance which influence the resonator characteristics of the line systems 53' and 53", and therefore influence the signal supplied to the signal outputs 67' and 67".

Further variants which illustrate the flexibility of the line system provided by the invention are shown in FIGS. 14, 15a), and 15b).

FIG. 14 shows a planar structure or line system 53''' which is comparable to that illustrated in FIG. 13a). The elements illustrated in FIG. 14 which correspond to the elements of the line system 53 in FIG. 13a) have the same reference numerals, except that they are followed by three apostrophes. As shown in FIG. 14, the shape of the line system 53''' may be adapted to a shape that is dictated by the geometry of the material 69''' to be measured. In comparison to the line system 53' illustrated in FIG. 13a), the signal input 65''' and the signal output 67''' are not spatially separated from one another. This is achieved by short-circuiting the line system 53''' at the opposite end from the signal input 65''' via a line (not illustrated). This means that a capacitor plate 59''' which closes off the line system 53''' is connected to the ground 55''' via an additional line having essentially negligible ohmic and inductive resistance. This allows evaluation of signals reflected back at the signal input 65'''. The adaptation to the shape of the material 69''' to be investigated may be carried out, for example, by designing the ground 55''' as an elastically deformable component. Thus, an important characteristic is the ability to adapt the resonators formed by the elementary cells to shaped surfaces.

As shown in FIGS. 15a) and 15b), the line systems according to the invention may also be manufactured in a planar shape by the same technique used for manufacturing conventional printed circuit boards. In the line system 73 illustrated in FIG. 15a), conductive regions 77 are formed on a substrate 75 using appropriate masking, etching, and/or coating processes. The regions 77 act as charging elements or capacitor plates which are separated from one another by gaps 79. The regions 77 are also connected to contact studs 81, in particular in the form of microstrip lines. The middle three contact studs 81 are connected via contacts 83, which act as inductive elements, to a grounding surface provided on the back side of the substrate 75 and not illustrated in FIG. 15a, whereas the outer contact studs are connected to a signal input 85 or signal output 87 of the line system 73. Thus, the contacts 83 act as feedthroughs for the grounding surface (not illustrated). When a medium 89 is provided on the substrate 75 in the regions 77 or is led over these regions, the line system 73 allows the characteristics or parameters of the medium to be determined in the manner described above. In the line system 73' illustrated in FIG. 15b), essentially spiral-shaped regions 77' are provided on a substrate 75'. These regions are connected at appropriate locations to a ground situated on the back side of the substrate 75' via contacts (not illustrated) which act as inductive elements. As the result of a respective interruption or gap 79', the spiral-shaped regions 77' represent multiple capacitive elements on a line path from a signal input 85' to a signal output 87'. This line system 73' as well may be used to determine the characteristics of a medium 89' applied in the regions 77' or led over the regions 77'.

Thus, it is possible to produce planar as well as shape-conforming structures for implementing the present invention, which are important characteristics with regard to flexibility, mechanical stability, and production costs.

FIG. 16 illustrates a further possible configuration for implementing a device according to the invention which includes an inverse line resonator for measuring the permeability. Using the configuration or line system 95 shown in FIG. 16, it is possible to measure the diamagnetic properties of solid bodies in the form of a cylindrical pin as well as of powdered materials. For this purpose the line system 95 includes capacitive elements 101 connected in series between a signal input 97 and a signal output 99, each capacitive element being situated in an elementary cell 103. In addition, the capacitive elements 101 in each elementary cell 103 are connected via inductive elements in the form of coils 105 to a common ground 107 to form an LC oscillating circuit or an LH line. To measure the characteristics or parameters of a medium 109, if it is a solid body, in particular having an essentially cylindrical shape, the medium is inserted into the coils 105. For a fluid medium 109, a cylindrical tube may be inserted inside the inductive elements 105, through which the medium 109 is then conducted.

The transmission characteristics of a balanced RHLH line are illustrated in FIG. 17. The graph shown in FIG. 17 depicts simulation data. The absolute value of the output signal is plotted versus the frequency of the supplied signal. Transmission maxima, which are characteristic for the individual resonance modes n of the line system, are identifiable in the figure. The transmission characteristics of the zeroth-order resonance mode (circled in FIG. 17) are not a function of the value of the resistances, and thus of the losses of the material to be investigated. The transmission characteristics for measurements using materials experiencing great losses allow no further resonance mode to be unambiguously detected besides the zeroth-order resonance mode, for example. Such a system may be used, for example, to investigate materials having relatively high dielectric or also diamagnetic losses.

Thus, mixed right- and left-handed line systems (RHLH lines) may be operated in zeroth-order resonance mode (zeroth-order resonator). This resonance mode exists only for the RHLH lines. The most important characteristics of this mode are as follows:

The resonance frequency of the line system is independent of the physical and electrical dimensions of the resonator, The LH characteristics of the RHLH line have opposite directions for the phase and group velocity, The quality of the resonator in this case is independent of the number of unit cells, thus allowing use of very compact line systems.

In principle, the above-described line systems may be used to investigate the dielectric as well as the diamagnetic properties of any given materials in the microwave range, provided that the materials can be machined so that they fit in the particular device. In particular by making use of the characteristics of zeroth-order resonance it is also possible to investigate materials with high dielectric or diamagnetic losses. The only limitation of the above-referenced method is that a microwave field must be able to propagate into the material being investigated. This is not a problem for electrically conductive materials, for example.

Depending on the shape of the materials or media to be investigated (solid, powdered, or also a specially shaped), a line resonator or line system according to the invention may be specifically adapted to the problem at hand. In principle, fluids, i.e., gaseous or liquid media, in particular are considered as a "material" or medium, provided that the fluids and gases have differing dielectric or diamagnetic properties from air or vacuum.

FIGS. 18a) and 18b) show a further possible application of multiple left-handed line resonators using the line systems or devices according to the invention. FIG. 18a) shows a cross-sectional view of a further line system 111 according to the invention, whereas FIG. 18b) shows the circuitry principle of the elements of the line system 111 and illustrates the cylindrical shell as a surface, the cross-sectional view of FIG. 18a) being shown along plane C-C in FIG. 18b). The line system 111 includes an essentially cylindrical resonator structure provided around a tube 113 in which a medium 117 to be investigated is placed, or through which the medium 117 is conducted. The resonator structure comprises a grounding surface 115, which surrounds the tube 113 essentially coaxially, i.e., in particular is designed as a grounding tube, and charging elements, i.e., capacitor plates 119, provided in the region of an outer wall of the tube 113 and connected to the grounding surface 115 via wires 121 which act as inductors. As shown in FIG. 18b), "rings" of capacitor plates 119 are situated at equidistant intervals along the tube 113. For the line system illustrated in FIGS. 18a) and 18b), four line resonators are shown on a dielectric tube. The distinctive feature of this system is the fact that in this case not only are each of the four oppositely situated line structures which are formed by respective pairs of capacitor plates, for which the respective electrical fields 123 are shown in FIG. 18a), in resonance, but also all line structures form line resonators with one another. The resonance frequencies of the "additional" resonators are shifted with respect to the resonance frequencies of the oppositely situated resonators.

By skillful dimensioning and evaluation of the output signals of the entire resonance structure, it is possible to determine the permittivity of the medium 117 in the tube 113 as well as the distribution of the medium 117 over the cross section. This is particularly advantageous when the medium 117 which flows through the measuring tube 113 forms strands, which heretofore have been detectable only to a limited extent using conventional material density sensors. The information concerning the material density over the cross section is obtained by correlation of the measured signals.

FIGS. 19 and 20 illustrate a further device according to the invention which includes a line system. FIG. 19 shows a cross-sectional view of the schematic design which implements a further inverse LH resonator, and FIG. 20 shows a perspective view. The line system illustrated in FIG. 19 includes capacitor plates 131 situated at opposite sides of a dielectric tube 133 which may be made of plastic, glass, or ceramic. The capacitor plates have a suitable shape, in particular which corresponds to the surface of the tube 133. In addition, the capacitor plates 131 are positioned in such a way that pairs of oppositely situated capacitor plates 131 are offset with respect to one another, in particular along a longitudinal direction of the tube 133. The capacitor plates 131 are also connected via short inductive elements 135 to an outer tube 139 contacting a ground 137. A high-frequency signal 143 in the microwave range is supplied via a connector 141, in particular via a coaxial cable attached to the connector 141. When a coaxial cable is used, the internal conductor of the coaxial cable is connected to one of the inductive elements 135. As described in the previously illustrated embodiments, the microwave signal is led through the resonator, i.e., line structure, and is coupled out as a signal 147 at the other side by means of an additional connector 145, which likewise may be attached to a line which in particular is coaxial. On the basis of the transmitted high-frequency signal 147 it is then possible to measure the frequency and phase shift of the signal, which is influenced by the dielectricity and permittivity of a material or medium 149 which is present in the tube 133 or which is conducted through the tube 133 in the region of the measuring path specified by the dimensions of the line system. As described above, from these signals the material density and material distribution in the material 149 may be calculated, in particular by use of a suitably programmed computer (not shown). As previously described, FIG. 20 shows a perspective view of an implementation of the line system illustrated in cross section in FIG. 19, but with the outer tube 139 omitted.

The evaluation of a signal received by a line system according to the invention is explained below, with reference to various graphs.

The difference in the signal conductance for a conventional resonator having a standard, i.e., RH, line and a resonator or line system according to the invention having an inverse, i.e., LH, line, is explained with reference to FIG. 21. This figure graphically illustrates the transmission through a conventional RH line system and an LH line system according to the invention, as a function of the signal frequency. The much narrower shape of the resonance maxima for the inverse or LH line is particularly noticeable in this diagram. When a design according to the invention using inverse lines is used, a slight detuning of the resonator structure as a result of a dielectric material causes a great change in the transmission, and therefore in the signal to be measured. As a result of this effect, the sensitivity of a design according to the invention is increased considerably compared to that of a conventional design. The appearance of harmonic resonances with negative order coefficients (in FIG. 20 n=−3, −2, and −1) is typical when inverse lines are used. The invention in particular allows a measurement for resonances having comparatively large negative order coefficients.

For an LH line system according to the invention, FIG. 22 shows the absolute value of the output signal ($|S_{21}|$, left ordinate) as a function of the signal frequency and the phase angle ($s_{21}$, right ordinate) between the signal current and the signal voltage for the case that a line system according to the invention is empty or filled with air, and for the case in which a medium, where $\in_r \neq 1$, interacts with the line system. FIG. 22 in particular illustrates the difference in absolute values of the signal from an empty and from a filled inverse resonator structure according to the invention. For a filled resonator, i.e., the filled line system according to the invention (dashed line), the resonance frequencies are shifted to lower frequencies compared to the empty inverse resonator according to the invention. This is illustrated in FIG. 22 using an example of the minus-third-order resonance maximum (also see FIG. 21). Whereas the third-order maximum is shifted by only 1.8 MHz, corresponding to a relative shift of the maximum by approximately 0.2%, introduction of the material into the resonator according to the invention at the fixed resonance frequency of the minus third harmonic of the unfilled resonator results in a 60° phase shift of the signal. The curves relating to the right ordinate are characterized by a jump from −180° to 180° in the range of 750 MHz. Thus, analysis of the signal supplied by a line system according to the invention may be performed most easily by analyzing the phase angle of the signal at given resonance orders. At these locations, analysis of the phase shift in the output signal allows a very accurate determination of the characteristics of the material to be investigated.

FIG. 23 shows a diagram which graphically illustrates the measured phase angle ($S_{21}$) as a function of time, measured using a design according to the invention corresponding to FIG. 19 and FIG. 20. For this measurement, millet was led through the tube 133 in batches. The clearly identifiable change in the phase angle toward negative values, whereby the phase angle was measured at a third-order resonance. This change in the phase angle is best measured in the third mode of the line system, and the characteristics of the millet result in the phase shift, whereby from the absolute value of the phase shift it is possible to determine the relative dielectricity of the millet, and if this parameter is known, also to determine the density distribution.

The apparatus which receives the signal illustrated in FIG. 23 is shown in the disassembled state in FIG. 24. Used as the tube 133 in this case is a glass tube 151, for example composed of a low-loss material such as borosilicate glass, for example as marketed by Schott under the trademark Duran®. The charging elements, i.e., capacitor plates 131, provided in the form of copper plates 153 are mounted on the glass tube. Inductive elements 135 in the form of metal pins 155 soldered to the copper plates 153 are provided on the copper plates 153. The metal pins 155 may include silver wires, for example. In this case a metal pipe 157 in which the assembly comprising the glass tube 151, copper plates 153, and metal pins 155 is installed is used as the outer tube 139 which forms a common ground. The assembly is stabilized by use of two flanges 159 which are fastened to the actual test apparatus via four threaded rods 161 and screw nuts 163. The signal is extracted using two coaxial connectors 165, which as connectors 141, 145 are used to inject into or extract from the line system. In particular, the connection of respective coaxial lines (not illustrated) to the coaxial connectors via coaxial plugs allows the internal conductors thereof to be connected to external metal pins 155 for injecting and extracting the signal, whereas the external conductor for the coaxial cable may be connected to the outer tube and thus to the common ground. This results in a further reduction of interference and noise signals. The openings in the glass tube 151 allow the material 149 which is to be measured to be led through the line system or introduced into same. In the assembled state, the apparatus shown in FIG. 24 has a length of approximately 300 mm, for example, with the measuring path having a length of approximately 230 mm, for example. The glass tube 151 may have a diameter of approximately 32 mm, for example, for accommodation or passing through of a material or medium to be investigated. The medium or material may be conducted through the apparatus at a mass throughput of 0.5 to 1.5 kg/h, for example.

FIG. 25 shows a perspective view of the schematic design of a further device according to the invention which is largely composed of the elements illustrated in FIG. 24. The interior of the tube 151 is visible through a cutout. At that location the direction of motion of the medium 149 is indicated by an arrow 166. The outer shell of the tube is a metal pipe 157 which functions as a ground. The metal pipe 157 has a diameter of 60 mm, for example. The signal 143 is injected through the two coaxial lines 167, and after passing through the material 149 the signal 147 is extracted. The measured variable may be determined from the two signals. This may be carried out, for example, by determining the difference between the two signals. By means of suitable programming, evaluation may also be automatically carried out by an integrated circuit. Such a processor is ideally connected to a display device, such as a monitor, for example, or a speech output device, which indicates to a user of the device according to the invention the material distribution or the type of material 149.

FIGS. 26a) and 26b) illustrate a schematic cross-sectional view of the device of FIGS. 24 and 25, designed as a microstrip resonator. As previously explained, the resonator in the form of a CRLH sensor illustrated in FIGS. 24 through 26b) allows the material density of a medium 149 conducted through the glass tube 151 to be determined. The CRLH sensor is composed of a dielectric conveying tube in the form of the glass tube 151 having an internal diameter d$_i$, which may be in the range of 32 mm, for example. Metal-insulator-metal (MIM) LH capacitors which include the copper plates 153 are situated around the tube 151; the sensor also includes wire LH inductors in the form of the metal pins 155 between the capacitor plates in the form of the copper plates 153 and the ground which is represented by the metal pipe 157. The metal pipe 157 has a diameter d$_0$ of approximately 60 mm Stray RH capacitors are present between the LH capacitor plates and the ground, and leakage RH inductors are present along the LH capacitor plates. FIG. 26b) shows a section of an MIM capacitor illustrated in FIG. 26a). FIG. 26b) illustrates in particular the course of the electrical field 168 between the copper plates 153.

FIG. 27 illustrates the absolute value of the output signal $|S_{21}|$ as a function of a signal frequency as received in a measurement, together with the results of a simulation of the circuit of the device according to the invention shown in FIGS. 24 through 26b). It is seen that there is very good agreement between the measured values and the simulation values.

The following discussion describes the manner in which the data measured on a device according to the invention may be used to determine a material density as a parameter of a medium conducted through the line system or provided in same. As previously described, a change in the permittivity of the medium or in the density of the medium, in particular a solid in particle form, which is introduced into the measuring path, i.e., line system, results in a change in the capacitance of the line system and thus a change in the resonance frequency of the line system. The phase gradient reaches its maximum value in the vicinity of the resonance frequency and initially remains constant, so that the change in the resonance frequency is proportional to the phase shift of the line system, i.e., the phase shift between an input signal and an output signal. A material density ρ is a function of the average value of the measured phase shift $\phi_{meas}$ (t). The average value may be determined either by integration of function $\phi_{meas}$ (t) over time, or from the null value of the Fourier transform of $\phi_{meas}$ (t). Using the phase shift $\phi_0$ (t) of the empty or air-filled device and the quality Q of the empty or air-filled measuring path, the effective absolute permittivity may be estimated by $$\varepsilon'_{r,eff} \approx \left(1 - \frac{\varphi_0 - \varphi_{meas}}{Q_L}\right)^{-2}. \tag{14}$$

The concentration α of solid particles in a solid/air mixture conducted through the line system of the measuring path may be defined as $$\alpha = \frac{V_{MUT}}{V_{Air} + V_{MUT}} \tag{15}$$

where $V_{MUT}$ is the volume of the solid and $V_{AIR}$ is the volume of the air in the mixture.

Assuming that $\varepsilon'_{r,eff}$ is a linear function of the concentration of the solid, the following expression is obtained:

$$\varepsilon'_{r,eff} = \varepsilon'_{r,MUT} \cdot \alpha + \varepsilon'_{r,Air} \cdot (1-\alpha). \tag{16}$$

When the specific density $\rho_{MUT}$ of the bulk material for solid particles is known, the integral of the material density may be calculated as follows:

$$\varrho_{eff}(t) \approx \varrho_{MUT} \cdot \frac{\varepsilon'_{r,eff} - \varepsilon'_{r,Air}}{\varepsilon'_{r,MUT} - \varepsilon'_{r,eff}}, \tag{17}$$

where $\varepsilon_{r,MUT}$ is the permittivity of the bulk material and $\varepsilon_{r,AIR}$ is the permittivity of the air conducted through the measuring path.

The design and mode of operation of an evaluation unit for a device according to the invention is explained below with reference to FIG. 28. This evaluation unit in particular allows the device according to the invention to be used as a mass flow sensor having increased sensitivity compared to conventional microwave mass flow sensors. A device 200 according to the invention, whose design is illustrated in FIG. 28 in the form of a block diagram, includes in particular a CRLH resonator having a line system 202. A mass flow 203 of a medium flows through the line system 202. A signal detection range of the device 200 also includes a high-frequency source 204 which generates a high-frequency signal which is split into two signals by a power splitter 205, one signal being supplied to the line system 202 and the other signal being supplied to a phase shifter 206. The high-frequency signal picked up at the output of the line system 202 is sent to an input of a phase detector 208. The output signal of the phase shifter 206 is also supplied to the phase detector 208. The phase shifter 206 may in particular be calibrated in such a way that when the line system 202 is empty or filled with air, a phase difference between the signals supplied to the phase detector 208 is zero.

When particles flow through the line system 202, a phase shift which is different from zero is detected. The phase detector 208 sends a phase difference as a function of time φ(t). The average value of the function φ(t) contains the material density information, whereas the function φ(t) also contains velocity information concerning the mass flow 203. To determine these values, the output signal of the phase detector 208 is supplied to a transformation unit 210, by means of which in particular a Fourier transformation of the function φ(t) is performed.

The output signals of the transformation unit 210 are supplied to two evaluation units 211, 213. In a first evaluation unit 211 an averaging unit 212 is used to determine a density in the form of the function ρ(t) as a first parameter of the medium conducted through the line system 202. For this purpose, the signal obtained from the transformation unit 210 is relayed to the unit 212 via a low-pass filter. The reason is that the density information is contained specifically in the direct current portion of the output signal of the line system. By use of the second evaluation unit 213, the function v(t), i.e., the velocity of the mass flow 203 through the line system 202, is determined in a signal processing unit 214 as the second parameter of the medium conducted through the line system 202. The signal of the transformation unit 210 passes through a high-pass filter, since the velocity information is contained specifically in the alternating current portion of the output signal of the line system. Knowledge of the functions ρ(t) and v(t) allows the mass flow to be determined as function m (t) as a function of time t, using a third evaluation unit in the form of a signal postprocessing unit 216.

Thus, in the example of an evaluation unit illustrated in FIG. 28, a signal recognition unit which detects a particle flow in a line system determines a mass flow; a first evaluation unit is used to determine a time-dependent density of the medium which by means of the mass flow 203 passes through the line system 202, whereas a second evaluation unit determines the velocity of the mass flow 203.

Since the procedure for determining the material density ρ(t) has been previously described, one possibility for determining the velocity information v(t) as carried out by the evaluation unit 213 is described below.

To determine the velocity of an object or a particle flow using the device according to the invention, the shift of the complex transmission function $S_{21}$ for a resonance mode may be investigated by use of a monofrequency signal. For example, to this end the third resonance mode of a resonator according to the invention may be used. Each time an object reaches a capacitor for the resonator, i.e., line system 202, the transmitted high-frequency signal, i.e., the output signal of the line system 202, approximately describes a sinusoidal curve which begins at 0° when the object enters the capacitor and ends at 180° when the object exits the capacitor. A spatial filtering velocity measurement uses the fundamental frequency of this influence on the line system. This frequency is a function of the physical parameters of the line system 202, and is proportional to the velocity of the object passing through the line system.

A further possibility for determining the velocity involves the use of autocorrelation.

The method used in the device 200 is based on the concept of the laser Doppler velocity measurement technique, except that the measurement apparatus is much less complex. Thus, a laser Doppler velocity measurement requires an extensive measuring system and two coherent lasers to achieve satisfactory results. In the spatial filtering velocity measurement an optical system is used which includes a light source, wherein an object to be measured passes through a light beam from the light source. The light beam strikes a spatial filter, in particular via a lens, and after passing through the spatial filter strikes a photodetector. When the object passes through the light beam, due to the spatial, periodic permeability of the spatial filter as the result of the object shadow a periodic output signal is generated at the photodetector. This output signal, in particular the frequency of the periodic output signal, contains information concerning the velocity of the object. Two examples of illuminated spatial filters which are illuminated on the basis of grid lines for the velocity measurement in a $\vec{e}_u$ direction are illustrated in FIGS. 29a) and 29b). FIGS. 29a) and 29b) show the manner in which the intensity of the light received by the photodetector periodically varies over time. The signal thus received is a function of the velocity $v=v_0 \cdot \vec{e}_u$ of the moving object and the characteristics of the spatial filter. Thus, for example, the grid in FIG. 29a) results in a rectangular signal, whereas the grid in FIG. 29b) results in a sinusoidal signal.

When this method is used for the device according to the invention, it is seen that the field distribution within the line system 202 exhibits a quasi-sinusoidal characteristic. FIG. 29 [sic; 30a)] shows an equivalent circuit diagram of a line system according to the invention and the corresponding field distribution of the high-frequency field, in a side view. FIG. 30b) shows a top view of the field distribution. As a result of the spatial filtering effect, the design of the device according to the invention, in particular the line system, allows the velocity of an object or mass flow moving through the line system to be determined in the manner described below. For this purpose, instead of a voltage signal of a photodetector a power signal of the line system is evaluated.

The spatial filtering effect used in the invention is based on the following theoretical principle:

Assuming that f (x, y) is the field intensity distribution of the object moving through the line system in the x-y plane, and h (x, y) is the transmission function of the spatial filter distribution, the signal g ($x_r$, $y_r$) emitted from the line system is obtained from a convolution integral to give the following:

$$g(x_r, y_r) = \int \int_{-\infty}^{\infty} f(x_r - x, y_r - y) h(x, y) dx dy, \quad (18)$$

It is assumed that the object moves at a velocity $\vec{v} = v_x \cdot \vec{e}_x + v_y \cdot \vec{e}_y$, and the expressions $x_r = v_x t + c_1$ and $y_r = v_y t + c_2$ are valid, where $c_1$ and $c_2$ are constants.

Assuming that the field intensity distribution f (x, y) follows a stationary ergodic process in two dimensions, the Fourier transforms of the autocorrelation function of g($x_r$, $x_r$) may be written as $$G_p(\mu, v) = F_p(\mu, v) H_p(\mu, v). \quad (19)$$

Due to the fact that in the device according to the invention, i.e., the line system 202, mass flow 203 occurs essentially in one spatial direction, for example along an x axis, it may be assumed that the particles move along the x axis at a velocity $\vec{v} = v_x \vec{e}_x$, i.e., $v_\rho = 0$. Therefore it is sufficient when the transmission h (x, y) of the spatial filter is periodic in the x direction and uniform in the y direction. Thus, the power spectral density function $G_p$ (f) may be derived by integration of formula (19) over the spatial frequency v to give the following:

$$G_p(f) = \frac{1}{|\vec{v}|} \int_{-\infty}^{\infty} F_p\left(\frac{f}{|\vec{v}|}, v\right) H_p\left(\frac{f}{|\vec{v}|}, v\right) dv \quad (20)$$

The relationship $\mu = f/|\vec{v}|$ is used, and f is the frequency in the time domain.

The periodic transmission function of the velocity measurements in one direction is given by $$h(x, y) = h(x) = h(+mp) \quad (21)$$

The entire power spectrum of the transmission function may be derived from $$H(\mu, v) = X^2 Y^2 |H_Y(v)|^2 |H_x(\mu)|^2 |H_c(\mu)|^2 |H_s(\mu)|^2 \quad (22)$$

$X^2 Y^2$ is the distribution of power as the result of the window region of the spatial filter. $|H_Y(v)^2|$ and $|H_X(\mu)|^2$ are the Fourier transforms of the rectangular functions resulting from the dimensions (in the x and y directions) of the spatial filter, i.e., the window region. $|H_c(\mu)|^2$ results from the periodicity in the interval p of the transmission function. $H_s(\mu)|^2$ is obtained from the Fourier transforms of one period of the transmission h(x), and represents the distribution of the transmission within a slit. Assuming that sinusoidal transmission is present, h(x) is given by $$h(x) = \frac{1}{2}\left(1 + \cos\frac{2\pi}{p} x\right). \quad (23)$$

The power spectrum is then given by $$|H_{s1}(\mu)|^2 = \left(\frac{\sin \pi \mu p}{\pi \mu p}\right)^2 \left(\frac{1}{2(1 - \mu^2 p^2)}\right)^2 \quad (24)$$

The frequency component which is selected when $\mu=1/p$ provides periodic signals having a temporary frequency $f=\mu v=v/p$. The frequency may be used to determine the velocity. To this end, the frequency f at which the power spectrum has a maximum value is determined. The power spectrum also contains higher harmonics for uneven multiples of the frequency f, these maximum values being greatly attenuated. Thus, an analysis of the power spectrum allows determination of the position of the maximum values in the spectrum in the frequency domain, and according to the previous equation this position of the maximum values allows the velocity v of the object to be determined. If multiple objects are moving at different velocities through the line system, the power spectrum in the frequency domain has multiple maximum values, each maximum lying at a frequency which corresponds to the respective velocity of the object.

As illustrated in FIG. 28, on the basis of the theoretical relationships stated above the material density and material velocity may be determined as follows:

First, the measured continuous signal $\phi(t)$ is transformed into the frequency domain $\Phi_n$, using a discrete Fourier transformation. A high-pass filter may suppress the direct current portion, which contains the material density information. It should be noted that the high-pass filter must have a sharp segment edge so that only the frequency portions in the power spectrum which contain density information are masked, while the frequency portions in the power spectrum which contain velocity information are allowed to pass through. For example, for a resonator length of less than 1 m and a velocity of 10 m/s, the maximum value in the power spectrum is exactly 10 Hz. Alternatively, for using a high-pass filter the direct current portions in the output signal of the line system may also be suppressed. For this purpose the average value of the output signal in the time domain may be subtracted from the output signal of the line system before carrying out the Fourier transformation. The presence of a fundamental mode $f_p$ and harmonics in the frequency domain $\Phi_n$ indicate flow through the line system. The velocity may be determined by $$v = \frac{f_p}{2} \cdot \frac{L_{sens}}{c}, \quad (25)$$

where $L_{sens}$ is the length of the measuring path, i.e., is essentially the length of the line system, and c is the number of maximum values obtained when a single object passes through the line system or the sensor.

When the influence of a single object during its passage through the line system is known, the autocorrelation of the high-pass filtered phase $\phi_h(t)$, as previously described, shows various maximum values in addition to the primary maximum. FIG. 31 illustrates the curve of an autocorrelation function $\phi_h(t)$ for a third resonance mode of the resonator when a single object passes through the line system. As expected, the primary maximum occurs at $\tau=0$. The signal periodicity results in additional maximum values which contain the velocity information. Use of the autocorrelation function allows detection of a large number of objects simultaneously passing through the line system and determination of the respective velocity of each object.

In summary, the present invention provides a sensor, i.e., a device, for determining various parameters of a medium. A sensor is provided which in particular allows a density of the medium as well as a velocity of the medium to be determined, and which therefore may be used as a mass flow sensor. The sensor is based on a CRLH resonator, i.e., a composite right-handed/left-handed transmission line resonator (CRLH-TL resonator). Compared to microwave sensors, which use frequencies that lie in the range of a segment frequency of a conducting unit, the line system of the invention may be operated at lower frequencies. In contrast to known sensors, for the device according to the invention there is also no conflict of goals between the sensor length or resonator length and the operating frequency, so that a sensor which is compact, operates at low frequencies, and has satisfactory measurement accuracy may be provided for detecting small changes in the permittivity.

The spatial filtering velocity measurement allows the material velocity or the velocity of the medium to be detected using a single sensor. In this regard the measurement accuracy of the velocity measurement is essentially specified by the characteristics of the signal processing unit or the evaluation unit and the characteristics of the spatial filter.

The features disclosed in the above description, in the drawings, and in the claims may be essential for implementation of the invention, alone or in any given combination. In particular it is noted that the invention is not limited to the embodiments described in the exemplary embodiments. Thus, for example, differing geometric shapes of the elements may be used, and in particular the shape of the described tubes is not limited to a circular cross section. Thus, polygonal, for example triangular, square or rectangular, elliptical, oval, or other cross sectional shapes may also be used.

| LIST OF REFERENCE SIGNS | |
|---|---|
| 1 | Measuring system |
| 3 | Tube |
| 5 | Medium |
| 7a, 7b | Capacitor plate |
| 9 | Ground |
| 11a, 11b | Line |
| 13 | Network analyzer |
| 15 | Electric field |
| 17 | Material sample |
| 19 | Capacitor assembly |
| 21a, 21b | Capacitor plate |
| 23 | Coil assembly |
| 25 | Winding |
| 27 | Line resonator |
| 29a, 29b | Line |
| 31a, 31b | End |
| 33a, 33b | Coil |
| 35a, 35b | Path |
| 37a, 37b | Connector |
| 39a, 39b | Connector |
| 41a, 41b | Capacitor |
| 43a, 43b | Ground |
| 45b | Coil |
| 47b | Capacitor |
| 49 | Resistor |
| 51 | Resistor |
| 53, 53', 53'', 53''' | Line system |
| 55, 55', 55'', 55''' | Grounding |
| 57 | Elementary cell |
| 59, 59', 59'', 59''' | Capacitor plate |
| 61, 61', 61'', 61''' | Wire |
| 63, 63', 63'' | Capacitor |
| 65, 65', 65'', 65''' | Signal input |
| 67, 67', 67'', 67''' | Signal output |
| 69', 69'', 69'''' | Material |
| 71', 71'' | Electric field line |
| 73, 73' | Line system |
| 75, 75' | Substrate |
| 77, 77' | Region |
| 79, 79' | Gap |
| 81 | Contact stud |
| 83 | Contact |
| 85, 85' | Signal input |

-continued

| LIST OF REFERENCE SIGNS | |
|---|---|
| 87, 87' | Signal output |
| 89, 89' | Medium |
| 95 | Line system |
| 97 | Signal input |
| 99 | Signal output |
| 101 | Capacitive element |
| 103 | Elementary cell |
| 105 | Coil |
| 107 | Grounding |
| 109 | Medium |
| 111 | Line system |
| 113 | Tube |
| 115 | Grounding surface |
| 117 | Medium |
| 119 | Capacitor plate |
| 121 | Wire |
| 123 | Electric field line |
| 131 | Capacitor plate |
| 133 | Tube |
| 135 | Inductive element |
| 137 | Ground |
| 139 | Outer tube |
| 141 | Connector |
| 143 | Signal |
| 145 | Connector |
| 147 | Signal |
| 149 | Medium |
| 151 | Glass tube |
| 153 | Copper plate |
| 155 | Metal pin |
| 157 | Metal pipe |
| 159 | Flange |
| 161 | Threaded rod |
| 163 | Screw nut |
| 165 | Coaxial connector |
| 166 | Direction of medium flow |
| 167 | Coaxial line |
| 168 | Electrical field |
| 200 | Device |
| 202 | Line system |
| 203 | Mass flow |
| 204 | High-frequency source |
| 205 | Power splitter |
| 206 | Phase shifter |
| 208 | Phase detector |
| 210 | Transformation unit |
| 211 | Evaluation unit |
| 212 | Averaging unit |
| 213 | Evaluation unit |
| 214 | Signal processing unit |
| 216 | Signal postprocessing unit |
| A | Axis |
| B, C | Direction |
| $f_0$ | Resonance frequency |
| $\epsilon$ | Dielectric constant |
| $d_i, d_o$ | Diameter |

The invention claimed is:

1. A device comprising:
a measuring path having a line system that includes at least two elementary cells situated along the measuring path, each elementary cell comprising an electrical path from at least one input to at least one output, wherein the elementary cells each comprise at least one capacitive element;
a generator for generating an electrical or electromagnetic signal that is supplied to the input of a first elementary cell, the output of the first elementary cell being connected to the input of a second elementary cell such that said first and second elementary cells are connected in series, and the capacitive element of the respective first and second elementary cells being situated in the electrical path of the first and second elementary cells, and in each case at least one inductive element connects the electrical path of the first elementary cell and the second elementary cell to an electrical ground; and
an evaluation device for analyzing an output signal of the measuring path,
wherein the evaluation device is configured to determine at least one parameter of a medium that is introduced into the measuring path such that an electrical property of the capacitive element of an elementary cell is modified by the medium, and
wherein an electromagnetic field is coupled into and/or out of the medium by introducing the electrical or electromagnetic signal into the measuring path.

2. The device according to claim 1, wherein a dimension of at least one elementary cell is smaller than a wavelength of the electrical or electromagnetic signal or a wavelength of the electromagnetic field.

3. The device according to claim 1, wherein the at least one parameter of the medium includes a relative dielectric constant, a relative permeability constant, a type of the medium, a density distribution or density of the medium, a distribution of the medium in the measuring path, a velocity of the medium in the measuring path, a quantity flow or mass flow of the medium through the measuring path, or a phase state of the medium.

4. The device according to claim 1, wherein the medium that is introduced into the measuring path has at least one form selected from a group consisting of a fluid form, a solid form, a gaseous form, and a two-phase form, including liquid-gaseous, liquid-liquid, liquid-solid, gaseous-solid, solid-solid, gaseous-gaseous, or liquid-gaseous-solid form.

5. The device according to claim 1, wherein the medium is movable relative to the line system.

6. The device according to claim 1, wherein the measuring path further includes at least one conducting unit for conducting the medium, and wherein the line system is provided on a surface of the conducting unit such that the electromagnetic field is injected into the medium.

7. The device according to claim 6, wherein the conducting unit has, at least in places, a cross-sectional shape that is circular, oval, elliptical, triangular, square, rectangular, or polygonal, or segments of these cross sections including a circular segment or ellipsoidal segment.

8. The device according to claim 6, wherein the conducting unit includes at least one of a dielectric and diamagnetic material, a synthetic material, and an elastically or plastically deformable material.

9. The device according to claim 6, wherein the medium is provided in or conducted through the conducting unit.

10. The device according to claim 9, further comprising a conveying unit that operates by one of hydraulic, pneumatic, magnetic, or gravitational means via which the medium is conducted through the conducting unit.

11. The device according to claim 6, wherein the conducting unit is movable relative to the line system.

12. The device according to claim 1, wherein the electrical or electromagnetic signal is a high-frequency signal that is introduced into the measuring path or a high-frequency electromagnetic radiation that is coupled into the medium.

13. The device according to claim 1, wherein at least one output of the generator is connected to at least one input of the electrical path of the first elementary cell using a coaxial cable, and wherein at least one conductor of the coaxial cable is connected to the electrical ground.

14. The device according to claim 6, wherein the line system includes at least one capacitive element comprising a first charging element and a second charging element in the form of at least one pair of capacitor plates, and wherein the first and second charging elements are situated on at least one side facing away from the medium, on a surface of the conducting unit that includes at least one of an electrically conductive material, a semiconductor material, and a polymeric material.

15. The device according to claim 14, wherein the electromagnetic field is generated between the first and the second charging element and wherein the electromagnetic field is generated between charging elements of different elementary cells.

16. The device according to claim 14, wherein the medium is situated between the first and second charging elements.

17. The device according to claim 14, wherein the first and second charging elements are situated opposite from one another in a parallel manner.

18. The device according to claim 14, wherein the first and second charging elements are offset relative to each other along at least one longitudinal axis of the conducting unit.

19. The device according to claim 1, wherein the line system further comprises a third elementary cell, the capacitive element of the third elementary cell being situated in the electrical path of the third elementary cell,
wherein at least one inductive element connects the electrical path of the third elementary cell to the electrical ground, wherein the third elementary cell is inserted between the first and second elementary cells such that an input of the electrical path of the third elementary cell is connected in series to the output of the electrical path of the first elementary cell in place of the second elementary cell, and wherein an output of the electrical path of the third elementary cell is connected in series to the input of the electrical path of the second elementary cell.

20. The device according to claim 19, wherein the device includes a plurality of third elementary cells, wherein an output of the electrical path of one third elementary cell is connected in series to an input of the electrical path of another third elementary cell.

21. The device according to claim 19, wherein at least two of the first, second, or third elementary cells or a combination thereof are periodically oriented toward one another.

22. The device according to claim 1, wherein at least one input of the evaluation device is connected to at least one output of the electrical path of the second elementary cell or at least one output of the generator using a coaxial cable, wherein at least one conductor of the coaxial cable is connected to the electrical ground.

23. The device according to claim 22, wherein an input of the evaluation device is connected to the input of the electrical path of the first elementary cell using coaxial cable, and wherein at least one conductor of the coaxial cable is connected to the electrical ground and/or the output of the electrical path of the second elementary cell is connected to the electrical ground.

24. The device according to claim 1, wherein the evaluation device compares an electrical or electromagnetic input signal that is present at the input of the electrical path of the first elementary cell with an electrical or electromagnetic output signal that is present at the output of the electrical path of the second elementary cell or with an electrical or electromagnetic signal that is present after passing at least partially through the line system.

25. The device according to claim 24, wherein the evaluation device detects at least one absolute value of an amplitude, at least one phase, or at least one phase angle, of the at least one electrical or electromagnetic input signal or of the at least one electrical or electromagnetic output signal.

26. The device according to claim 25, wherein at least one phase angle change between the at least one electrical or electromagnetic input signal and the at least one electrical or electromagnetic output signal is detected.

27. The device according to claim 1, wherein the evaluation device includes at least one processor unit and at least one visual or acoustic output device for outputting the determined parameter of the medium.

28. The device according to claim 1, wherein the evaluation device includes a first evaluation unit for determining a first parameter of the medium and a second evaluation unit for determining a second parameter of the medium.

29. The device according to claim 28, wherein the evaluation device further includes a third evaluation unit for determining a third parameter of the medium based on the first and second parameters of the medium.

30. The device according to claim 28, wherein the evaluation device further includes at least one transformation unit for transforming the electrical or electromagnetic output signal of the measuring path and at least one comparative signal determined by a comparison of the input signal of the measuring path with the electrical or electromagnetic output signal of the measuring path, and wherein the first evaluation unit and the second evaluation unit are operatively connected to the transformation unit, and the first evaluation unit and the second evaluation unit are connected to the measuring path via the transformation unit.

31. The device according to claim 1, wherein at least one input of an elementary cell and at least one output of at least one additional elementary cell are directly connected to one another in series.

32. The device according to claim 1, wherein the electrical or electromagnetic signal is supplied via at least one input or at least one output of at least one elementary cell, and an output signal is extracted at the same input or output of the at least one elementary cell.

33. The device according to claim 19, wherein at least one inductive element of the first, second, and/or third elementary cell includes at least one conductor.

34. The device according to claim 6, wherein the elementary cells are associated with the conducting unit along at least one longitudinal direction and/or at least one radial direction.

35. A method for determining at least one parameter of a medium by using a device according to claim 1, the method comprising:
introducing the medium into a measuring path that includes a capacitive element that interacts with the medium, wherein the at least one parameter is determined based on at least one change in at least one electrical property of the capacitive element;
supplying a high-frequency input signal to the measuring path to generate within the measuring path at least one zeroth-order and/or negative-order harmonic electromagnetic oscillation;
determining at least one amplitude, at least one phase angle change, and/or at least one phase angle of the oscillation after the input signal passes through the measuring path; and
determining the parameter of the medium based on the determined amplitude, phase angle, or phase angle change.

36. The method according to claim 35, wherein the input signal is supplied to a line system comprising a series connection of at least two elementary cells, each elementary cell having at least one capacitive element and at least one inductive element, wherein the capacitive elements of the at least two elementary cells are connected in series and the inductive elements of the at least two elementary cells connect the capacitive elements to an electrical ground.

37. The method according to claim 35, wherein an absolute value of an amplitude and/or phase angle between the current and voltage of the oscillation is determined, and wherein the parameter of the medium is determined by a time-based comparison of the input signal and an output signal of the measuring path or by a time-based comparison of a first electromagnetic oscillation without influence of the medium on the measuring path and a second electromagnetic oscillation with the influence of the medium on the measuring path.

38. The method according to claim 35, wherein pneumatically conveyed dust-like materials comprising an organic material, an inorganic material, liquids, bodily fluids, or a bulk material are used as the medium.

39. The method according to claim 35, further comprising transforming at least one of an output signal of the measuring path and a comparative signal into a transformed signal, wherein the comparative signal represents a phase difference and is obtained by comparing the input signal and the output signal of the measuring path.

40. The method according to claim 39, further comprising using a first evaluation unit to determine a first parameter of the medium based on at least one of the output signal of the measuring path, the input signal of the measuring path, the comparative signal, and the transformed signal.

41. The method according to claim 40, further comprising using a second evaluation unit to determine a second parameter of the medium based on at least one of the output signal of the measuring path, the input signal of the measuring path, the comparative signal, and the transformed signal.

42. The method according to claim 41, further comprising filtering at least one of the output signal of the measuring path, the input signal of the measuring path, the comparative signal, and the transformed signal using at least one filter unit included in the first evaluation unit or the second evaluation unit.

43. The method according to claim 42, wherein the first parameter is determined based on an average value of the output signal of the measuring path, the input signal of the measuring path, the comparative signal, the transformed signal, the filtered output signal of the measuring path, the filtered input signal of the measuring path, the filtered comparative signal, and/or the filtered transformed signal, and wherein the second parameter is determined based on a maximum value of the output signal of the measuring path, the input signal of the measuring path, the comparative signal, the transformed signal, the filtered output signal of the measuring path, the filtered input signal of the measuring path, the filtered comparative signal, and/or the filtered transformed signal.

44. The method according to claim 41, further comprising using a third evaluation unit to determine a third parameter of the medium based on the first parameter and the second parameter.

45. The method according to claim 35, wherein the at least one parameter of the medium is a relative dielectric constant, a relative permeability constant, a type of the medium, a density distribution or density of the medium, a distribution of the medium in the measuring path, a velocity of the medium in the measuring path, a quantity flow or mass flow of the medium through the measuring path, or a phase state of the medium.

46. The method according to claim 43, wherein the maximum value is at least one of a maximum point of a function, a magnitude of a maximum value, and a number of maximum values, the maximum value being determined by at least one time-based derivation or a derivation according to a frequency.

47. The device according to claim 12, wherein the high-frequency signal is a microwave signal or millimeter wavelength signal, and the high-frequency electromagnetic radiation is microwave radiation or millimeter wavelength radiation.

48. The device according to claim 14, wherein the first and second charging elements are situated on opposite sides of the conducting unit.

49. The device according to claim 25, wherein the at least one phase angle change is detected between the voltage and current.

50. The device according to claim 28, wherein the first parameter of the medium is a density of the medium and the second parameter of the medium is a velocity of the medium.

51. The device according to claim 29, wherein the third parameter of the medium is a quantity flow or mass flow of the medium through the measuring path.

* * * * *